US008883853B2

(12) United States Patent  (10) Patent No.: US 8,883,853 B2
Kaplan  (45) Date of Patent: *Nov. 11, 2014

(54) N-SUBSTITUTED BENZENEPROPANAMIDE OR BENZENEPROPENAMIDE DERIVATIVES FOR USE IN THE TREATMENT OF PAIN AND INFLAMMATION

(75) Inventor: Eliahu Kaplan, Petah Tiqwa (IL)

(73) Assignee: Novaremed Limited, Petah Tiqwa (IL)

( * ) Notice: Subject to any disclaimer, the term of this patent is extended or adjusted under 35 U.S.C. 154(b) by 188 days.

This patent is subject to a terminal disclaimer.

(21) Appl. No.: 12/921,004

(22) PCT Filed: Mar. 6, 2009

(86) PCT No.: PCT/IB2009/000448
§ 371 (c)(1),
(2), (4) Date: Nov. 2, 2010

(87) PCT Pub. No.: WO2009/109850
PCT Pub. Date: Sep. 11, 2009

(65) Prior Publication Data
US 2011/0039936 A1  Feb. 17, 2011

(30) Foreign Application Priority Data

Mar. 6, 2008 (GB) .................................. 0804213.7

(51) Int. Cl.
*A61K 31/165* (2006.01)
*C07F 3/00* (2006.01)
(52) U.S. Cl.
CPC ............... *C07F 3/003* (2013.01); *A61K 31/165* (2013.01)
USPC .......................................................... 514/617
(58) Field of Classification Search
CPC ..................................................... A61K 31/165
USPC ......................................................... 514/617
See application file for complete search history.

(56) References Cited

U.S. PATENT DOCUMENTS

| | | | |
|---|---|---|---|
| 2,908,691 A | 10/1959 | Robinson | |
| 4,766,106 A | 8/1988 | Katre et al. | |
| 4,908,322 A | 3/1990 | Jacobson et al. | |
| 5,541,206 A | 7/1996 | Kempf et al. | |
| 5,585,397 A | 12/1996 | Tung et al. | |
| 7,642,290 B2 | 1/2010 | Kaplan | |
| 7,674,829 B2 | 3/2010 | Kaplan | |
| 8,252,843 B2 | 8/2012 | Kaplan | |
| 8,309,606 B2 | 11/2012 | Kaplan | |
| 2006/0135620 A1 | 6/2006 | Kaplan | |
| 2006/0148874 A1 | 7/2006 | Kaplan et al. | |
| 2009/0306214 A1 | 12/2009 | Kaplan | |
| 2011/0086910 A1 | 4/2011 | Kaplan | |

FOREIGN PATENT DOCUMENTS

| | | |
|---|---|---|
| CN | 101503370 A | 8/2009 |
| CN | 101503373 A | 8/2009 |
| EP | 0887340 A1 | 12/1998 |
| EP | 1876169 A1 | 1/2008 |
| GB | 1392674 A | 4/1975 |
| JP | 52036606 | 3/1977 |
| JP | H07101924 A | 4/1995 |
| WO | WO-9723202 A1 | 7/1997 |
| WO | WO-9729079 A1 | 8/1997 |
| WO | WO-0246176 A1 | 6/2002 |
| WO | WO-2004031129 A2 | 4/2004 |
| WO | WO-2005092305 A2 | 10/2005 |
| WO | WO-2007129226 A2 | 11/2007 |
| WO | WO-2009039218 A2 | 3/2009 |
| WO | WO-2009109850 A2 | 9/2009 |

OTHER PUBLICATIONS

The Richheimer Pain, 2000.*
Adamczyk et al., "Stereoselective *Pseudomonas cepacia* lipase mediated synthesis of α-hydroxyamides", *Tetrahedron: Asymmetry*, 8(15):2509-2512 (1997).
Nicolaus, B.J.R., "Symbiotic Approach to Drug Design", *Decision Making in Drug Research*, pp. 173-186 (1983).
Lee, et al. "Effects of Phenolic Acid Esters and Amides on Stimulus-Induced Reactive Oxygen Species Production in Human Neutrophils." Clinica Chimica Acta. 352(1-2), 135-141 (2005).
Park. "Caffedymine from Cocoa Has Cox Inhibitory Activity Supressing the Expression of a Platelet Activation Marker, P-Selectin." Journal of Agricultural and Food Chemistry. 55(6), 2171-2175 (2005).
Marquez, et al. "Anti-inflammatory Evaluation and Phytochemical Characterization of Some Plants of the *Zanthoxylum* Genus." ACTA Farmaceutica Bonaerense. 24(3), 325-330 (2005).

(Continued)

*Primary Examiner* — Shailendra Kumar
(74) *Attorney, Agent, or Firm* — Mintz Levin Cohn Ferris Glovsky and Popeo, P.C.; Shovon Ashraf

(57) ABSTRACT

Compounds for use in the treatment or prophylaxis of pain, including acute and chronic pain (e.g., nociceptive pain, neuropathic pain, headaches, migraine), represented by general formula (I) in which: the dotted line represents a single or a double bond; and R5 and R5' are independently —H, —OH or —OR$_6$, where R$_6$ is a linear or branched C$_1$-C$_4$ alkyl; X is -0-, —CH$_2$O—, —CH$_2$CH$_2$O—, —CH(CH$_3$)CH$_2$O— or —CH$_2$CH(CH$_3$)O—; Z is —CH$_2$CH$_2$O—, —CH(CH$_3$)CH$_2$O— or —CH$_2$CH(CH$_3$)O—; m is an integer of 0 or 1; and n is an integer of 0-50. The compounds of the invention are also effective for reducing inflammation and may be used alone or in combination with other analgesics.

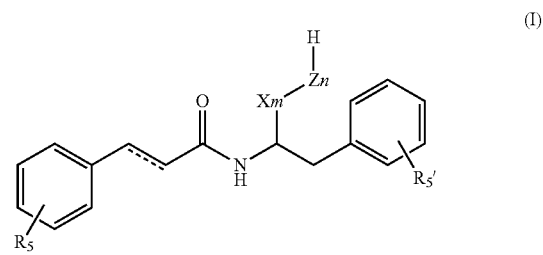

(I)

20 Claims, 6 Drawing Sheets

(56) References Cited

OTHER PUBLICATIONS

Amara et al. "Circulating Autoantibodies Directed Against Conjugated Fatty Acids in Sera of HIV-1-Infected Patients." *Clin. Exp. Immunol.* 96(1994):379-383.

Amat et al. "Sythesis of Enantiopure Trans-3,4-Disubstituted Piperidines. An Enantiodivergent Synthesis of (+)- and (−)-Paroxetine." *J. Org. Chem.* 65.10(2000):3074-3084.

Arutyunyan et al. "Synthesis of Pseudosparsomycins." *Pharm. Chem. J.* 23.10(1989):837-840. (English Translation Only).

Azzouz et al. "Selective Tetrahydropyranylation under Non-Acidic Conditions." *Synlett* 18(2005):2808-2810.

Beaulieu et al. "2',6'-Dimethylphenoxyacetyl: A New Achiral High Affinity P3-P2 Ligand for Peptidomimetic-Based HIV Protease Inhibitors." *J. Med. Chem.* 43.6(2000):1094-1108.

Braun et al. "New Oxidative Transformations of Phenolic and Indolic Oxazolines: An Avenue to Useful Azaspirocyclic Building Blocks." *J. Org. Chem.* 65.14(2000):4397-4408.

Braun et al. "Darstellung von Aldehyden and Ketonen mit Hilfe des Abbaues quartdrer Ammoniumbasen." *Chem. Ber.* 65.14(1929):235-241. (No English Available).

Burke et al. "Hydroxylated Aromatic Inhibitors of HIV-1 Integrase." *J. Med. Chem.* 38.21(1995):4171-4178.

Burke et al. "Small Hydroxylated Aromatic Inhibitors of HIV-1 Integrase as Potential Anti-AIDS Drugs." *NIH Conference on Retroviral Integrase Molecular and Pharmacology a Novel Target for the Treatment of AIDS.* (1995):1-2.

Bussolari et al. "Parallel Synthesis of 2-alkoxy and 2-acyloxyphenylpropyl Amides and Amines Using Dihydrocoumarins as Versatile Synthons. Application of a Novel Resin Quenchcapture Method." *Tetrahedron Lett.* 40.7(1999):1241-1244.

Caldirola et al. "New Prenylamine-Analogues: Investigations of Their Influence on Calcium-Dependent Biological Systems." *Eur. J. Med. Chem.* 28(1993):555-568.

Clark et al. "Some Substituted Phenethyl and 3-Phenylpropyl Styryl Ketones and the Corresponding Saturated Ketones." *J. Chem. Soc.* (1962):126-130.

Davyt et al. "A New Indole Derivative from the Red Alga *Chondria Atropurpurea.* Isolation, Structure Determination, and Anthelmintic Activity." *J. Nat. Prod.* 61.12(1998):1560-1563.

Detert et al. "Cationic Amphiphiles with G-protein-Stimulatory Activity: Studies on the Role of the Basic Domain in the Activation Process." *Pharmazie.* 51.2(1996):67-72.

Dumont et al. "Note on Attempts to Prepare Ring-B Homomorphinan-6-ones by Grewe Cyclization from Octahydro-1-phenethylisoquinolines." *Helvetica Chimica Acta.* 68.8(1985):2128-2131.

Glennon et al. "Influence of Amine Substituents on 5-HT2A versus 5-HT2C Binding of Phenylalkyl- and Indolylallcylamines." *J. Med. Chem.* 37.13(1994):1929-1935.

Greenfield et al. "Convenient Synthesis of Functionalized Terphenyls." *Tetrahedron Lett.* 44.13(2003):2729-2732.

Greenwald et al. "Highly Water Soluble Taxol Derivatives: 7-Polyethylene Glycol Carbamates and Carbonates." *J. Org. Chem.* 60(1995):331-336.

Heilbron et al. "CLXXVIL-Styrylpyrylium Salts. Part XIII. The Reactivity of Methyl P-Phenylethyl and Methyl 7-Phenylpropyl Ketones." *J. Chem. Soc.* pp. (1931):1336-1342.

Herbert et al. "The Biosynthesis of *Sceletium* Alkaloids in *Sceletium Subvelutinum* L. Bolus." *Tetrahedron.* 46.20(1990):7105-7118.

Hochstein. "Quantitative Studies on Lithium Aluminum Hydride Reactions." *J. Am. Chem. Soc.* 71(1949):305-307.

Horii et al. "Syntheses and Pharmacological Properties of 2- and 3-Arallcyltetrahydro-1,3-oxazines." *Chem. Pharm. Bull.* 13.10(1965):1151-1159.

Kamenecka et al., "Construction of Substituted Cyclohexanones by Reductive Cyciization of 7Oxo-2,8-alkadienyl Esters." *Organic Lett.* 4.1(2002):79-82.

Külz et al. "Über Synthesen spasmolytisch wirkender Stoffe. II. Mitteilung." *Chem. Ber.* 72(1939):2161-2166. (No English Available).

Kunishima et al. "Synthesis and Characterization of 4(4,6-Dimethxy-1,3,5-triazin-2-y1)-4-methylmorpholinium Chloride." *Tetrahedron Lett.* 40(1999):5327-5330.

Le Blanc et al. "New Access to Spiranic p-Lactams." *Tetrahedron Lett.* 33.15(1992):1993-1996.

Liang. "CXCR4, Inhibitors and Mechanisms of Action." *Chem. Biol. Drug Design.* 72(2008):97-110.

Lin et al. "Anti-Inflammatory Neolignans from Piper Kadsura." *J. Nat. Prod.* 69.5(2006):842-844.

Luly et al. "Modified Peptides which Display Potent and Specific Inhibition of Human Renin." *Biochem. Biophys. Res. Commun.* 143.1(1987):44-51.

Morisaki et al. "Synthesis of Novel Vitamin C Phosphodiesters: Stability and Antioxidant Activity." *Carbohydrate Res.* 286(1996):123-138.

Nesterenko et al. "Identification from a Combinatorial Library of a Small Molecule that Selectively Induces Apoptosis in Cancer Cells." *J. Am. Chem. Soc.* 125.48(2003):14672-14673.

Nivlet et al. "Reductive Opening of Cyclopropylogous a-Hydroxy Aldehydes and Ketones by Samarium(II) Iodide." *Tetrahedron Lett.* 39(1998):2115-2118.

Obora et al. "Palladium Complex Catalyzed Acylation of Allylic Esters with Acylsilanes." *J. Am. Chem. Soc.* 123.43(2001):10489-10493.

Ochiai et al. "Triphenylphosphine-Mediated Olefmation of Aldehydes with (Z)-(2-acetoxyalk-1-enyl)phenyl-k3-iodanes." *Chem. Commun.* 13(2000):1157-1158.

Park et al. "*N*-Caffeoyltyramine Arrests Growth of U937 and Jurkat Cells by Inhibiting Protein Tyrosine Phosphorylation and Inducing Caspase-3." *Cancer Lett.* 202.2(2003):161-171.

Paul et al. "Condensation de quelques ethers vinyliques heterocycliques avec l'acroleine et ses homologues." *Bull. Soc. Chim. Fr.* (1954): 672-678. (No English Available).

Rao et al. "Synthetic Studies in Polycyclic Systems: Part VP'- Syntheses of 3- Phenyl-, I-Methyl-3- phenyl- & 1,3-Diphenylphenanthrenes." *Ind. J. Chem.* 14B(1976):38-40.

Repke et al. "Synthesis of S(+) and R(−)-3-(2-Aminopropyl)indole from Ethyl-D- and L-Tryptophanate." *J. Heterocyclic Chem.* 13(1976):7775-7778.

Takeuchi et al. "Further Study on Effect of *N*-β-*phenylpropionyl-L-tyrosine* and its Derivatives on the Excitability of an Identifiable Giant Neuron of *Achatina fulica* Féerussac." *Comp. Biochem. Physciol. Part C.* 75C(2(1983):329-335. (Abstract Only).

Takeuchi et al. "Inhibitory Effects of Derivatives of L-Tyr and L-Trp on the Excitability of a Giant Neurone of African Giant Snail." *Neuropsciences* 7.1(1981):152-153. (Abstract Only).

Tamiz et al. "Structure-Activity Relationships for a Series of Bis(phenylalkyl)amines: Potent Subtype Selective Inhibitors of *N*-Methyl-D-aspartate Receptors." *J. Med. Chem.* 41.18(1998):3499-3506.

Treede et al. "Neuropathic Pain: Redefinition and a Grading System for Clinical and Research Purposes." *Neurology.* 70.18(2008):1630-1635.

Umino et al. "Sodium Acyloxyborohydride as New Reducing Agents. I. Reduction of Carboxamides to the corresponding Amine." *Tetrahedron Lett.* 10(1976):763-766.

von Karrer et al. "Δ3,5-Cholestadien-7-on aus Rindsleber." *Helvetica Chimica Acta.* 31.6(1948):1617-1623. (No English Available).

Yasuma et al. "Synthesis of Peptide Aledehyde Derivatives as Selective Inhibitors of Human Cathepsin L and their Inhibitory Effect on Bone Resorption." *J. Med. Chem.* 41.22(1998):4301-4308.

Zhao et al. "Arylamide Inhibitors of HIV-1 Integrase." *J. Med. Chem.* 40(1997):1186-1194.

\* cited by examiner

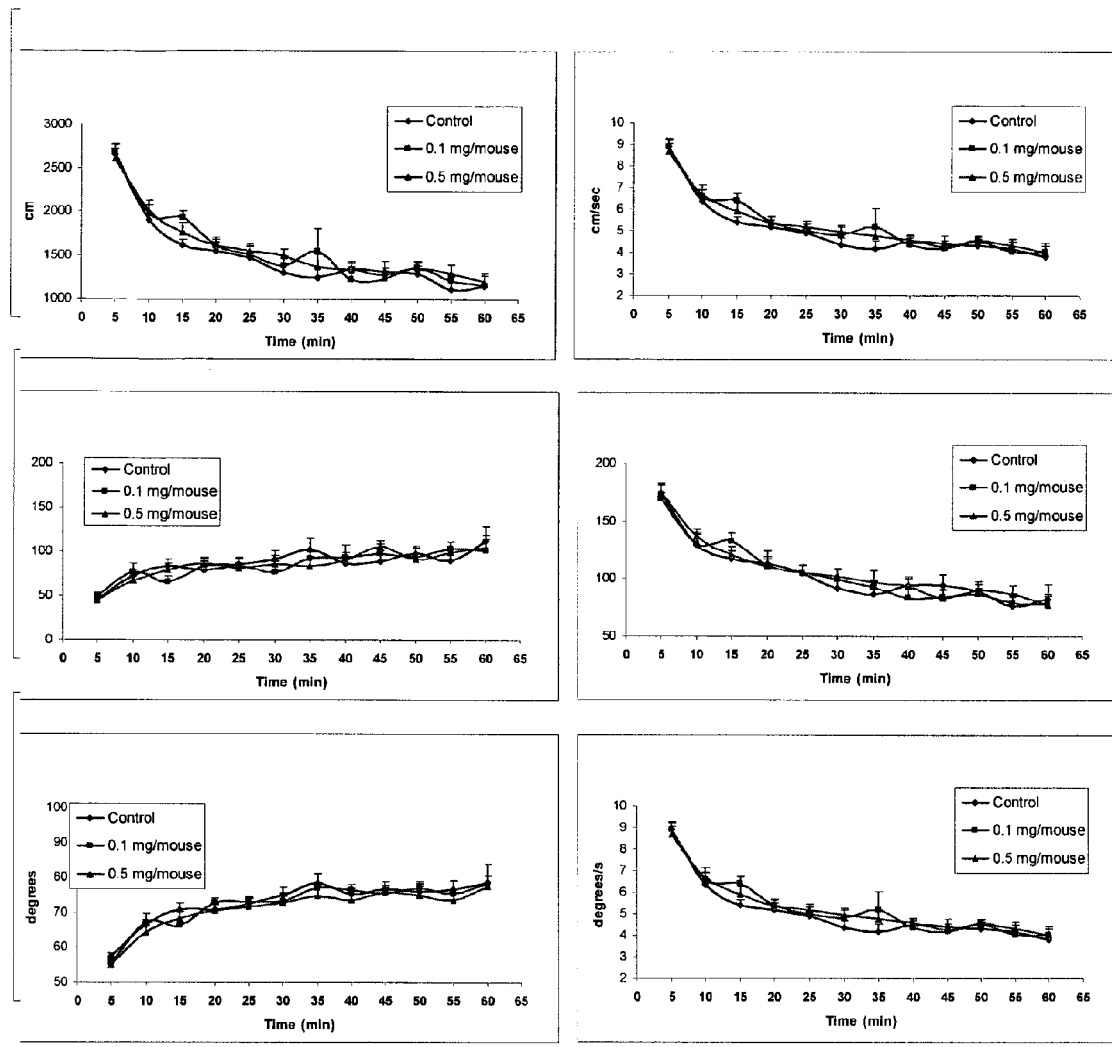
FIGS. 7A-F

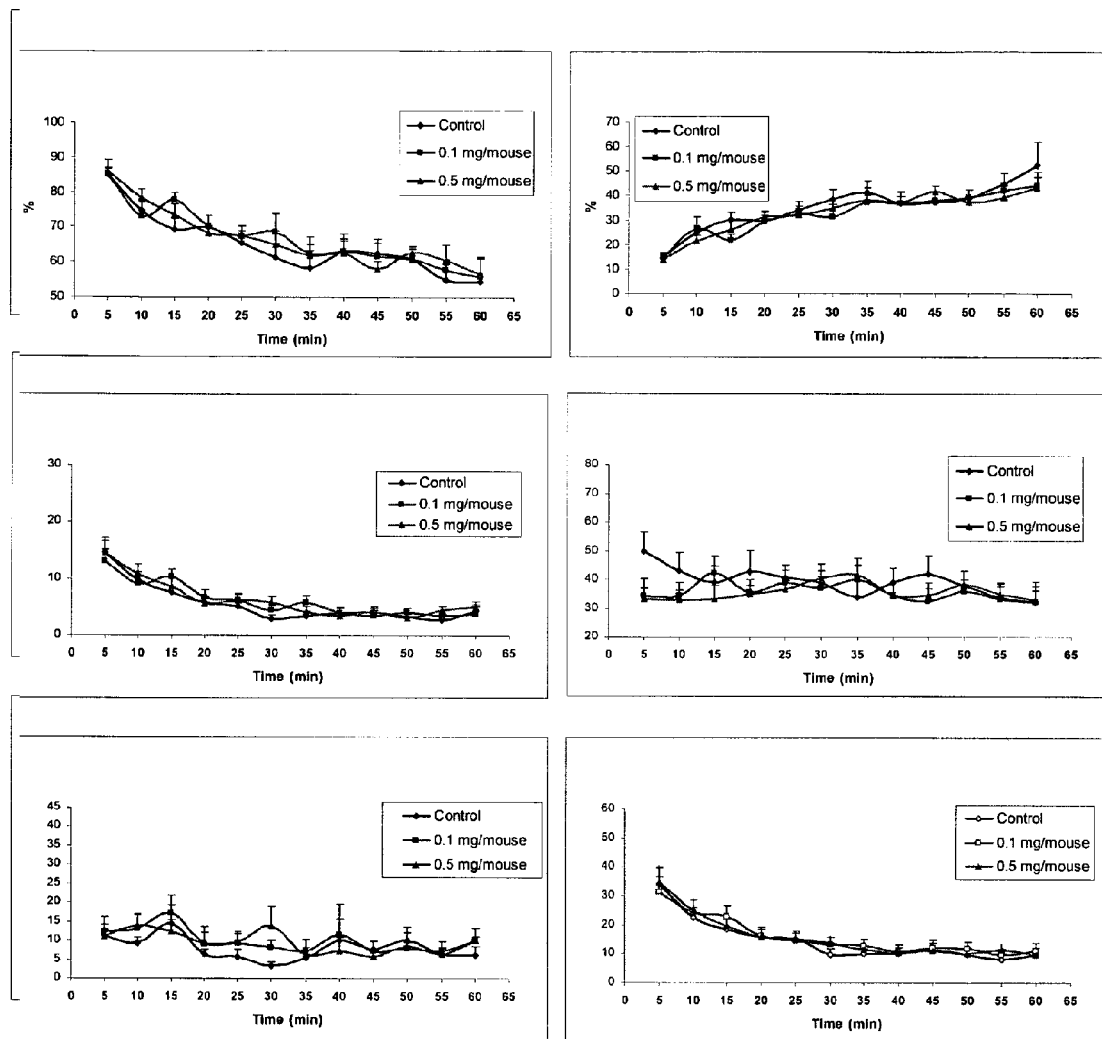
FIGS. 7G-L

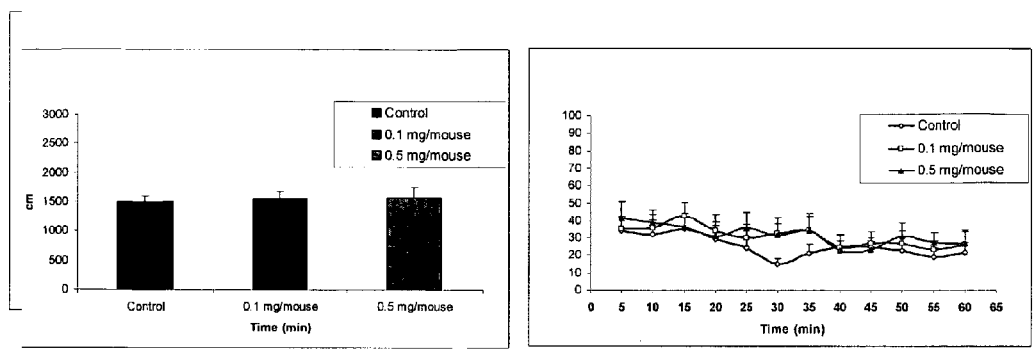
FIGS. 7M-N

N-SUBSTITUTED BENZENEPROPANAMIDE OR BENZENEPROPENAMIDE DERIVATIVES FOR USE IN THE TREATMENT OF PAIN AND INFLAMMATION

This application is a U.S. national stage application, filed under 35 U.S.C. 371, of International Application PCT/IB2009/000448, filed Mar. 6, 2009, which claims priority under 35 U.S.C. 120 to Great Britain Application No. 0804213.7, filed Mar. 6, 2008.

The present invention relates to the treatment or prophylaxis of pain and provides a method of treating or preventing pain as well as the use of certain compounds in the manufacture of medicaments for the treatment or prophylaxis of pain in humans and non-human animals.

Pain is a multifaceted or multidimensional, experiential response to a variety of stimulus conditions. Pain is defined by the International Association for the Study of Pain (IASP) as "an unpleasant sensory and emotional experience associated with actual or potential tissue damage, or described in terms of such damage".

Pain in animals is frequently the result of nociception, i.e., activity in the nervous system that results from the stimulation of nociceptors. Neuropathic pain differs from nociceptive pain in that it involves damage to the nerve resulting in the sensation of pain. In central pain, the pain is generated in the brain from some form of lesion. Occasionally pain may be psychogenic, i.e., caused by mental illness.

Pain can be acute or chronic. Acute pain is usually caused by soft tissue damage, infection and/or inflammation among other causes. Acute pain serves to alert after an injury or malfunction of the body. Chronic pain may have no apparent cause or may be caused by a developing illness or imbalance. Chronic pain is defined as the disease of pain; its origin, duration, intensity and specific symptoms may vary.

The experience of physiological pain can be grouped according to the source and related nociceptors. Cutaneous pain is caused by injury to the skin or superficial tissues. Cutaneous nociceptors terminate just below the skin, and due to the high concentration of nerve endings, produce a well-defined, localised pain of short duration. Examples of injuries that produce cutaneous pain include paper cuts, minor cuts, minor (first-degree) burns and lacerations. Somatic pain originates from ligaments, tendons, bones, blood vessels and nerves. It is detected with somatic nociceptors. The scarcity of pain receptors in these areas produces a dull, poorly-localised pain of longer duration than cutaneous pain; examples include sprains and broken bones. Myofascial pain is usually caused by trigger points in muscles, tendons and fascia and may be local or referred. Visceral pain originates from the body's viscera or organs. Visceral nociceptors are located within body organs and internal cavities. The even greater scarcity of nociceptors in these areas produces pain that is usually more aching and for longer duration than somatic pain. Visceral pain is extremely difficult to localise, and several injuries to visceral tissue exhibit "referred" pain, where the sensation is localised to an area completely unrelated to the site of injury. Phantom limb pain, a type of referred pain, is the sensation of pain from a limb that has been lost or for which a person no longer receives physical signals. Neuropathic pain may occur as a result of injury or disease to the nerve tissue itself. This can disrupt the ability of the sensory nerves to transmit correct information to the thalamus, and hence the brain interprets painful stimuli even though there is no obvious unknown psychological cause for the pain.

Acute pain is usually treated simultaneously with pharmaceuticals or appropriate techniques for removing the cause and pharmaceuticals or appropriate techniques for controlling the pain sensation, commonly analgesics.

Analgesics fall into three categories: opioid (narcotic) analgesics, non-opioid analgesics and adjuvant analgesics. Opioid analgesics are powerful analgesics that are chemically related to morphine. However, opioids have many side effects, which may be more likely to occur in people with certain disorders: kidney failure, a liver disorder, chronic obstructive pulmonary disease (COPD), dementia or another brain disorder. Drowsiness, constipation, nausea, vomiting and itching are common when opioids are started. Apart from morphine, opioid analgesics known at the time of writing include codeine, fentanyl, hydrocodone, hydromorphone, levorphanol, meperidine, methadone, oxycodone, oxymorphone, pentazocine and propoxyphene.

A variety of non-opioid analgesics are also available at the time of writing. They are often effective for mild to moderate pain. Most non-opioid analgesics are classified as non-steroidal anti-inflammatory drugs (NSAIDs). An example of an analgesic that is not an NSAID is acetaminophen, which is commonly known as paracetamol. Acetaminophen has substantially no anti-inflammatory properties.

NSAIDs are used to treat mild to moderate pain and may be combined with opioids to treat moderate to severe pain. NSAIDs not only relieve pain, but they also reduce the inflammation that often accompanies and worsens pain. Although widely used, NSAIDs can also have side effects, sometimes serious ones, including problems in the digestive tract, bleeding problems, problems related to retaining fluids and increased risk of heart and blood vessel disorders. Current NSAIDs include aspirin, ibuprofen, ketoprofen, naproxen, cox-2 inhibitors such as celecoxib, choline magnesium trisalicylate, diflunisal, salsalate, diclofenac, etodolac, fenoprofen, flurbiprofen, indomethacin, ketorolac, meclofenamate, mefenamic acid, meloxicam, nabumetone, oxaprozin, piroxicam, sulindac and tolmetin.

Adjuvant analgesics include antidepressants such, for example, as imipramine, amitriptyline, bupropion, desipramine, fluoxetine and venlafaxine; anticonvulsants (such as carbamazepine, gabapentin and pregabalin) and oral and topical local anaesthetics.

In the treatment of chronic pain, the "Three-Step Analgesic Ladder" developed by the World Health Organization is often used. For mild pain, acetaminophen, aspirin or other NSAIDs may be employed. For mild to moderate pain, week opioids such as codeine and dihydrocodeine are employed in combination with acetaminophen, aspirin or other NSAIDs. In the case of moderate to severe pain, strong opioids such as morphine, diamorphine, or fentanyl, hydromorphone, methadone, oxycodone or phenazocine may be administered in combination with acetaminophen, aspirin or other NSAIDs.

An object to the present invention is to provide alternative compounds for the treatment or prophylaxis of pain. In particular, it is object to the present invention to provide alternative NSAIDs for the treatment or prophylaxis of pain and to reduce inflammation. Desirably the compounds of the invention should have no or substantially no activity on the central nervous system.

Another object of the present invention is to provide an alternative method for the treatment or prevention of pain.

According to one aspect of the present invention therefore there are provided compounds for use in the treatment or prevention of pain, which compounds may be represented by general formula I below:

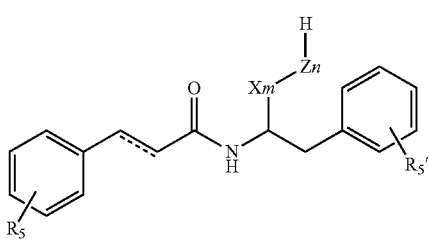

(I)

in which:

the dotted line represents a single or a double bond; and $R_5$ and $R_5'$ are independently —H, —OH or —$OR_6$, where $R_6$ is a linear or branched $C_1$-$C_4$ alkyl;

X is —O—, —$CH_2O$—, —$CH_2CH_2O$—, —$CH(CH_3)CH_2O$— or —$CH_2CH(CH_3)O$—;

Z is —$CH_2CH_2O$—, —$CH(CH_3)CH_2O$— or —$CH_2CH(CH_3)O$—; m is an integer of 0 or 1; and n is an integer of 0-50.

Suitably, said compounds may be the S-enantiomers of the compounds represented by formula I above. The invention also comprehends the use of the respective pharmaceutically acceptable salts and hydrates of the compounds of formula I.

The compounds of the present invention may be used for the treatment or prophylaxis of acute or chronic pain. For instance, the compounds may be used for the treatment of nociceptive pain such, for example, as cutaneous pain, somatic pain, myofascial pain, visceral pain, phantom limb pain or neuropathic pain. The compounds of the invention may also be used treatment of headaches or migraine. The compounds may be used alone or in combination with acetaminophen or another NSAID for the treatment of mild chronic pain or in conjunction with weak or strong opioids for the treatment of moderate or severe pain.

The compounds of the invention may also be employed in the treatment or prophylaxis of neuropathic pain and may be used in conjunction with one or more antidepressants or antiepileptic medicaments such, for example, as gabapentin or pregabalin.

According to another aspect of the present invention therefore there is provided a method for treating or preventing pain in a human or non-human animal patient, which method comprises administering to said patient in need thereof a therapeutic effective amount of one or more of the compounds of the invention.

For a human patient, a daily dose of 1.0 mg to 15 g of said one or more compounds in a pure, substantially pure or partially pure form as described in more detail below may suitably be administered. The compounds may be administered under the supervision of a medical practitioner in an amount sufficient to achieve effective pain management. In some embodiments, the daily dose of said one or more compounds may be titrated to determine such effective amount. Said daily dose may comprise about 5.0 mg to 1 g, typically about 5 mg to 500 mg. In some embodiments, said dose may comprise 10 mg to 100 mg per day of said one or more compounds. The compounds may be administered on a regimen of one to four times per day.

Said one or more compounds may be administered parenterally, transdermally, intramuscularly, intravenously, intradermally, intranasally, subcutaneously, intraperitoneally, intraventricularly or rectally. Preferably, the one or more compounds are administered orally.

Optionally, the one or more compounds of the present invention may be administered simultaneously, sequentially or separately with at least one opioid analgesic, an antidepressant or an antiepileptic medicament. Alternatively, the one or more compounds of the invention may be administered simultaneously, sequentially or separately with one or more other NSAIDs or acetaminophen.

In yet another aspect of the present invention there is provided the use of one or more of the compounds of the invention in the manufacture of a medicament for use in the treatment or prophylaxis of pain. Said medicament may be manufactured for co-administration with one or more of acetaminophen, another NSAID, an opioid, an antiepileptic or an antidepressant.

Advantageously, it has been found that the compounds of the present invention are effective for reducing or preventing inflammation. It has also been found that the compounds of the invention have no or substantially no (i.e., within acceptable limits) deleterious effect on the central nervous system.

As mentioned above, m may be 0; where m=0, n may be 1-50.

Alternatively, m may be 1.

X may be —$CH_2O$—.

In some embodiments of the invention, the compounds of the invention may be represented by general formula II below:

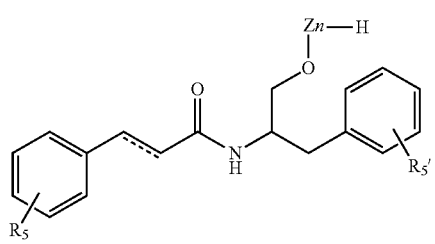

(II)

in which n, Z, $R_5$ and $R_5'$ are as defined above.

Z may be —$CH(CH_3)CH_2O$—.

In some embodiments of the present invention, the compounds of the invention may therefore be represented by general formula III below:

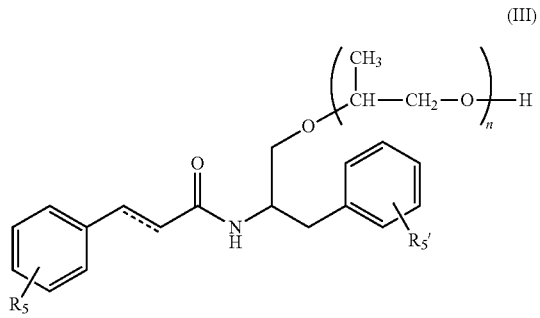

(III)

in which n, $R_5$ and $R_5'$ are as defined above.

$R_5$ may be H. Alternatively, $R_5$ may be OH.

$R_5'$ may be H. Alternatively, $R_5'$ may be OH.

Suitably, n may be an integer from 1-50, preferably 1-25. For example, n may be 1, 2, 3, 4, 5, 6, 7, 8, 9, 10, 11, 12, 13, 14, 15, 16, 17, 18, 19, 20, 21, 22, 23, 24 or 25. Advantageously, n may be 5-9 or 6-8, e.g., 7 or 15-19 or 16-18, e.g., 17.

Alternatively, the compounds of the invention may be the S-enantiomers of the compounds represented by general formulae IV, V, VI and VII below:

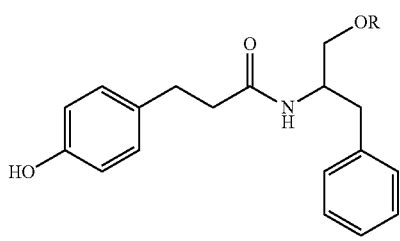
(IV)

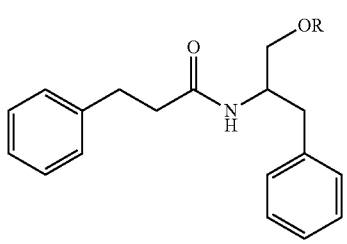
(V)

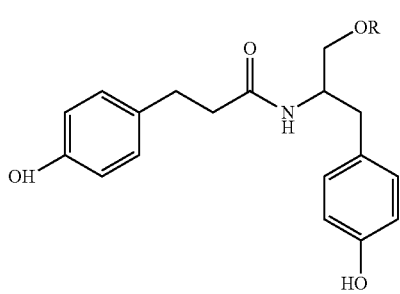
(VI)

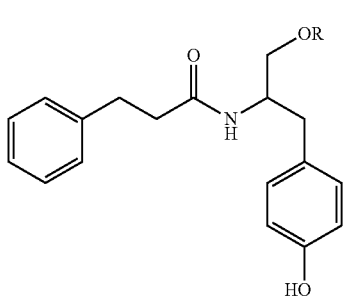
(VII)

in which R is a polyalkylene glycol polymer having n units, wherein n is as defined above, particularly n=1-50.

Suitably, said polyalkylene glycol polymer may be polyisopropylene glycol.

Suitable synthetic methods for obtaining and purifying the compounds of the present invention are disclosed in detail below. However, it should be apparent to a person skilled in the art that the compounds may be prepared using any other feasible synthetic methods.

The compounds of the invention may be synthesised as polyalkylene glycol (PAG) conjugates. Polymers that may be used for such conjugation include poly(ethylene glycol) (PEG), also known as or poly(ethylene oxide) (PEO) and polypropylene glycol (including poly isopropylene glycol).

A polyalkylene glycol (PAG), such as PEG, is a linear polymer terminated at each end with hydroxyl groups:

The above polymer, α,ω-dihydroxyl poly(ethylene glycol), can also be represented as HO-PEG-OH, where it is understood that the -PEG- symbol represents the following structural unit:

where p may range from 0 to about 48. PEG may be used as methoxy-PEG-OH, or mPEG, in which one terminus is the relatively inert methoxy group, while the other terminus is a hydroxyl group that is subject to ready chemical modification. Additionally, random or block copolymers of different alkylene oxides (e.g., ethylene oxide and propylene oxide) that are closely related to PEG in their chemistry may be substituted for PEG.

The PAG polymers may be linear or branched.

It is to be understood that compounds of the invention comprise a PAG moiety that may include a mixture of polymers which have a varying number of monomeric units. The synthesis of a PAG-conjugate compound may produce a population of molecules with a Poisson distribution of the number of monomeric units per polymer in the conjugate. Thus, a compound according to the invention that is described as having a polymer of n=7 monomeric units refers not only to the actual polymers in that population being described as having n=7 monomeric units, but also to a population of molecules with the peak of the distribution being 7 or close to 7. The distribution of monomeric units in a given population can be determined, e.g., by nuclear magnetic resonance (NMR) or by mass spectrometry (MS).

In yet another aspect of the present invention there is provided a pharmaceutical composition for use in the treatment or prophylaxis of pain, said composition comprising a pharmaceutically effective amount of one or more of the compounds of the invention. Said composition may further comprise one or more pharmaceutically acceptable excipients. In some embodiments, said composition may also comprise acetaminophen, one or more other NSAIDs, one or more weak or strong opioids, an antidepressant or an antiepileptic agent.

The pharmaceutical composition of the invention may comprise one or more of the compounds of the invention in a pure, substantially pure or partially pure form. In some embodiments, said substantially pure form may comprise at least 95% wt. of said one or more compounds, e.g., 96% wt., 97% wt., 98% wt. or more than 99% wt. of said compounds.

Said substantially or partially pure form of said compound(s) may further comprise a proportion of free polyalkylene glycol such, for example, as polyethylene glycol (PEG) or polypropylene glycol (PPG). Such polyalkylene glycol may itself be biologically active. The chain length of the free polyalkylene glycol may range from 1-50, preferably 1-25. In some embodiments, said polyalkylene glycol may have a chain length of 3, 7, 12 or 17 monomeric units. Said free polyalkylene glycol may comprise a mixture of different chain lengths. Thus, for a substantially pure form of said one or more compounds, said form may comprise up to 5% wt. of free polyalkylene glycol, e.g., up to 4% wt., 3% wt., 2% wt. or less than 1% wt., with the total amount in said form of said one or more compounds and said free polyalkylene glycol being 100% wt.

Said partially pure form of said one or more compounds may comprise about 5-60% wt. of the one or more compounds according to the invention and about 95-40% wt. of free polyalkylene glycol, the total amount being 100% wt. Typically, said partially pure form may comprise about 45-55% wt. of said one or more compounds and about 55-45% wt. of said one or more polyalkylene glycols. Alternatively, said form may comprise about 80-95% wt. of said one or more compounds and about 20-5% wt. of said polyalkylene glycol(s).

Suitably, the composition of the invention may be formulated as a unit dosage form. Each unit dosage form may comprise all or a predetermined fraction of the daily dose amount of the one or more compounds of the invention, e.g., one half or one quarter of the daily dose amount.

Thus, the composition may be formulated as a tablet, a pill, a capsule, a powder, granules, a sterile parenteral solution or suspension, a metered aerosol or liquid spray, drops, an ampoule, an auto-injector device, a suppository, a cream or a gel. Said composition may be adapted for oral, enteral parenteral, intrathecal, intranasal, sublingual, rectal or topical administration, or for administration by inhalation or insufflation. Oral compositions such as tablets, pills, capsules or wafers are particularly preferred.

For preparing a solid dosage form such as a tablet, said one or more compounds may be mixed with one or more pharmaceutical excipients, e. g., conventional tabletting ingredients such as corn starch, lactose, sucrose, sorbitol, talc, stearic acid, magnesium stearate, dicalcium phosphate or gums, or other pharmaceutical diluents, e. g., water, to form a solid pre-formulation composition containing a substantially homogeneous mixture of said one or more compounds, such that said one or more compounds are dispersed evenly throughout the composition, so that the composition may be readily subdivided into equally effective unit dosage forms such as tablets, pills and capsules.

Said solid pre-formulation composition is then subdivided into unit dosage forms of the kind mentioned above which may each contain from 0.1 to about 500 mg of the one or more compounds. Favoured unit dosage forms contain from 1 to 500 mg, e.g., 1, 5, 10, 25, 50, 100, 300 or 500 mg, of the compound(s).

When formulated as a tablet or pill, said tablet or pill may be coated or otherwise compounded to provide a dosage form affording the advantage of prolonged action. For instance, said tablet or pill can comprise an inner dosage and an outer dosage component, the latter being in the form of an envelope over the former. These two components may be separated by an enteric layer that serves to resist disintegration in the stomach and permits the inner component to pass intact into the duodenum or to be delayed in release. A variety of materials are known in the use in such enteric layers or coatings, such materials including a number of polymeric acids and mixtures of polymeric acids with such materials as shellac, cetyl alcohol and cellulose acetate.

Alternatively, the pharmaceutical composition of the present invention may be formulated as a liquid dosage form for administration orally or by injection; for example an aqueous solution, a suitably flavoured syrup, an aqueous or oil suspension or a flavoured emulsion with edible oils such, for example, as cottonseed oil, sesame oil, coconut oil or peanut oil, as well as an elixir or a similar pharmaceutical vehicle. Suitable dispersing or suspending agents for an aqueous suspension include synthetic and natural gums, e.g., tragacanth, acacia, alginate, dextran, sodium carboxymethylcellulose, methylcellulose, polyvinyl-pyrrolidone or gelatin.

Following is a description by way of example only with reference to the accompanying drawings of embodiments of the present invention.

Figure 1:
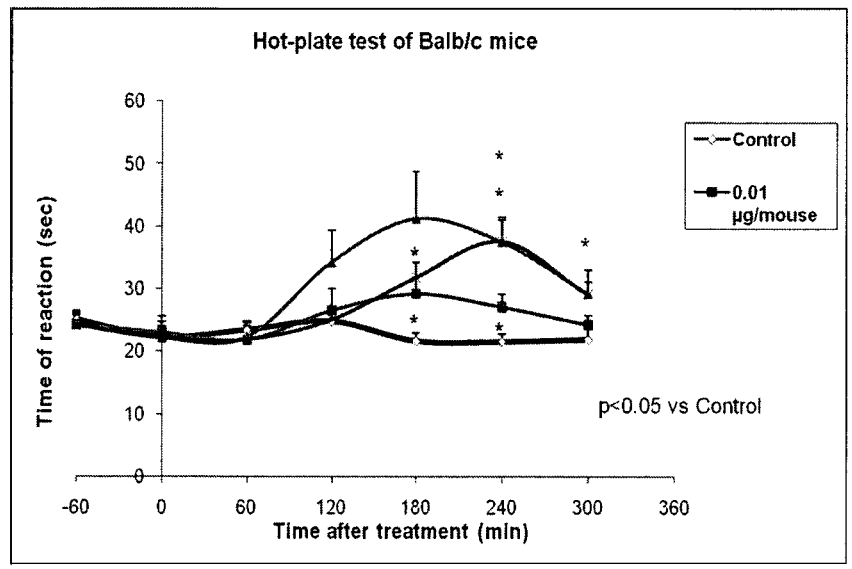
FIG. 1 is a graph showing the results of a Hot-Plate Test using Balb/c mice following administration of Compound 18 of the invention at 100 μg/mouse, 1 μg/mouse and 0.01 μg/mouse.

FIGS. 7A-N are a series of graphs respectively illustrating the following results of an Open Field Test after the administration of Compound 18 of the invention (0.1 mg/mouse, 0.5 mg/mouse; i.p., −60 min) to BALB/c mice:

A: distance moved (cm)

B: mean velocity

C: total duration of immobility

D: total duration of strong mobility

E: mean turn angle (degrees)

F: angular velocity (degrees/s)

G: total duration of movement (%)

H: total duration of non-movement (%)

I: in zone frequency (zone 3)

J: rearing frequency

K: in zone duration (zone 3)

L: in zone frequency (zones 2+3)

M: distance moved (cm)

N: in zone duration (zones 2+3)

Synthesis of Polyalkylene Glycol Compounds

Polyalkylene glycol compounds were generally synthesised by preparation of the appropriate alcohol compound (e.g., one of the compounds described in Synthesis 1 or a hydroxylated derivative thereof) followed by conjugation of the alcohol with a polyalkylene glycol (PAG) polymer (e.g., polyethylene glycol (PEG) or polypropylene glycol (PPG)) of the desired length.

Synthesis 1: Compound 1 (Phenyl Alaninol)

1.2 g, 32 mM, of $LiAlH_4$ were added to 2.3 g, 10 mM, phenyl alanine ethyl ester HCl in 50 ml dry ether. After stirring for 2 hours at room temperature, water and KOH were added and the reaction product was extracted with ethyl acetate. After evaporation, 0.8 g of Compound 1, a light yellow oil, was obtained.

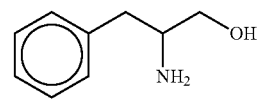

$C_9H_{13}NO$
Mol. Wt.: 151.21

Compound 1 crystallised on standing. Mp-70.

NMR $CDCl_3$ 7.30 (5H, m), 3.64 (1H, dd, J=10.5, 3.8 Hz) 3.40 (1H, dd, J=10.5, 7.2 Hz) 3.12 (1H, m), 2.81 (1H, dd, J=13.2, 5.2 Hz), 2.52 (1H, dd, J=13.2, 8.6 Hz)

NMR acetone $d_6$ 7.30 (5H, m), 3.76 (1H, dt) 3.60 (1H, m) 3.30 (1H, t), 2.85 (2H, m). *Helv. Chim. Acta*, 31, 1617(1948). Biels.-E3, Vol. 13, p 1757.

Synthesis 2: Compound 2 (Tyrosinol)

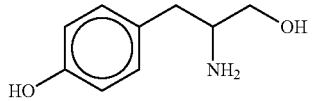

C$_9$H$_{13}$NO$_2$
Mol. Wt.: 167.21

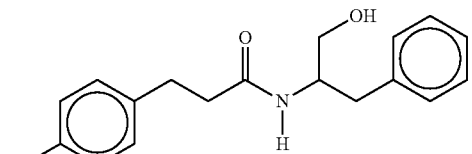

C$_{18}$H$_{21}$NO$_3$
Mol. Wt.: 299.36

To 3 g, 12 mM, L-tyrosine ethyl ester HCl in 50 ml dry ether was added 1.2 g 32 mM LiAlH$_4$. After stirring 3 hours at room temperature, water and KOH were added and the reaction was extracted with ethyl acetate. Evaporation gave 1.1 g of a light yellow oil, 54% yield, which on standing crystallized. mp-85.

NMR CDCl$_3$ 7.20 (4H, AB q, J=8.6 Hz), 3.50 (2H, m) 3.20 (1H, m), 2.81 (2H, m).

NMR tyrosine ethyl ester free base CDCl$_3$ 7.0, 6.56 (4H, AB q, J=8.8 Hz), 4.20 (2H, q, J=7, 0 Hz), 3.70, 3.0, 2.80 (3H, 12 line ABXm), 1.28. (3H, t, J=7.0 Hz). *JACS* 71, 305(1949). Biels.-E3, Vol. 13, p 2263.

Synthesis 3: Compound 3 (Tryptophanol)

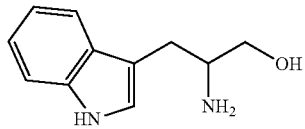

C$_{11}$H$_{14}$N$_2$O
Mol. Wt.: 190.24

To 3 g, 12.9 mM, L-tryptophan methyl ester HCl in 50 ml dry ether was added 1.2 g, 32 mM LiAlH$_4$. After stirring 6 hours at room temperature water and KOH were added and the reaction extracted with ethyl acetate. Evaporation gave 1.23 g light yellow oil, 50% yield. On standing crystallized. Mp-65.

NMR CDCl$_3$ 7.30 (5H, m), 3.64 (1H, dd, J=10.5, 3.8 Hz) 3.40 (1H, dd, J=10.5, 7.2 Hz) 3.12 (1H, m), 2.81 (1H, dd, J=13.2, 5.2 Hz), 2.52 (1H, dd, J=13.2, 8.6 Hz) *J. Het. Chem*, 13, 777 (1976). Biels.-E5, 22, Vol. 12, p 90.

Synthesis 4: Compound 4

0.66 g 4-hydroxy hydrocinnamic acid and 4 ml thionyl chloride in 30 ml cyclohexane were refluxed for 2 hours. After evaporation, a white solid was obtained, to which 0.65 g oil of Compound 1 (4.3 mM) in 30 ml dichloromethane and 0.4 ml triethyl amine were added. After stirring for 2 hours at room temperature, water and KOH were added in order to neutralize the pH. The reaction product was extracted with dichloromethane. Evaporation gave 0.8 g of Compound 4, light yellow viscous oil. Part of this product was triturated and recrystallized with ethanol to give a white solid. Mp-149.

NMR CDCl$_3$ 7.30-6.9 (9H, m), 3.50 (2H, m) 3.30 (2H, t, J=7.2 Hz) 2.90 (3H, m), 2.60 (2H, t, J=7.2 Hz).

Synthesis 5: Compound 5

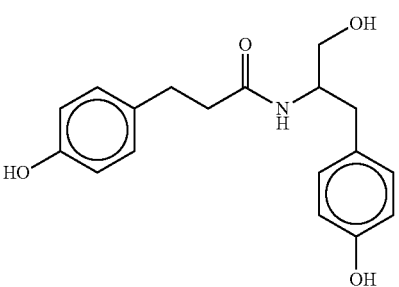

C$_{18}$H$_{21}$NO$_2$
Mol. Wt.: 283.36

0.75 g, 5 mM, hydrocinnamic acid and 4 ml thionyl chloride in 30 ml cyclohexane were refluxed for 2 hours. Evaporation gave a white solid to which were added 0.83 g, 5.5 mM, phenyl alaninol in 30 ml dichloromethane and 0.5 ml triethyl amine. After stirring 3 hours at room temperature, water and KOH were added to neutral pH and the reaction was extracted with dichloromethane. Evaporation gave 0.57 g of a yellow viscous oil, 40% yield.

NMR CDCl$_3$ 7.40-7.10 (10H, m), 3.60 (2H, m) 3.35 (2H, t, J=7.2 Hz) 2.95 (3H, m), 2.50 (2H, t, J=7.2 Hz).

Synthesis 6: Compound 6

C$_{18}$H$_{21}$NO$_4$
Mol. Wt.: 315.36

0.66 g, 4 mM, 4-hydroxy hydrocinnamic acid and 4 ml thionyl chloride in 30 ml cyclohexane were refluxed 3 hours. Evaporation gave a light yellow solid to which were added 0.72 g, 4.3 mM, tyrosinol in 30 ml dichloromethane and 0.5 ml triethyl amine. After stirring 3 hours at room temperature. water and KOH were added to neutral pH and the reaction was extracted with dichloromethane. Evaporation gave 0.53 g light yellow viscous oil, 42% yield.

NMR CDCl$_3$ 7.30, 7.20 (8H, 2 ABq, J=8.6 Hz), 3.40 (2H, m) 3.30 (2H, t, J=7.2 Hz) 2.90 (3H, m), 2.60 (2H, t, J=7.2 Hz).

Synthesis 7: Compound 8

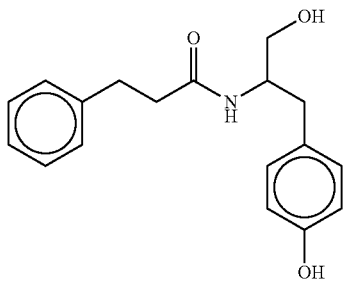

C₁₈H₂₁NO₃
Mol. Wt.: 299.36

0.45 g, 3 mM, hydrocinnamic acid and 3 ml thionyl chloride in 30 ml cyclohexane were refluxed for 2 hours. Evaporation gave a light yellow solid to which were added 0.58 g, 3.5 mM, tyrosinol in 30 ml dichloromethane and 0.4 ml triethyl amine. After stirring for 2.5 hours at room temperature, water and KOH were added to attain neutral pH and the reaction was extracted with dichloromethane. Evaporation gave 0.57 g light yellow viscous oil, 63% yield.

NMR CDCl₃ 7.40-7.10 (9H, m), 3.60 (2H, m) 3.35 (2H, t, J=7.2 Hz) 2.95 (3H, m), 2.50 (2H, t, J=7.2 Hz).

Synthesis 8: Compound 10

0.3 g of Compound 4, 0.8 g, triphenyl phosphine and 0.55 g ethyl diazo carboxylate were added to 1 g of poly(propylene glycol), (average molecular weight ca 1000), in 60 ml dichloromethane. Stirring for 2 hours at room temperature, evaporation and chromatography gave 0.65 g of Compound 10 as a viscous oil.

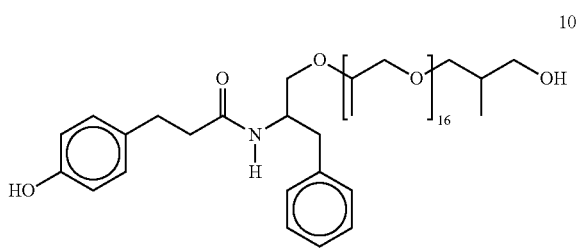

Compounds Synthesised from Phenyl Alaninol

These compounds include those represented by the structure of formula VIII:

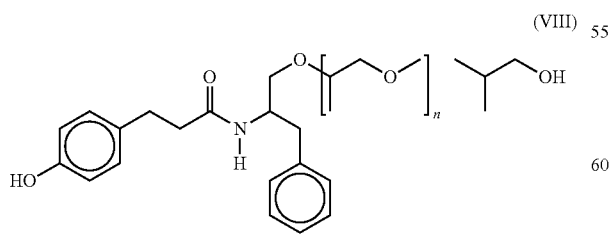
(VIII)

This compound can also be represented as formula A, where R is a polypropylene glycol polymer and n is the total number of polypropylene monomers in the polymer:

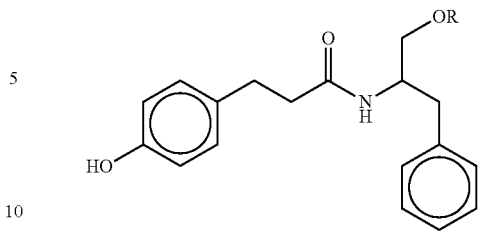
Formula A

Synthesis 9: Compound 11:
R=PPG (polypropylene glycol); n=7; MW=706

0.3 g Compound 4 (1 mM), 0.8 g, 3 mM, triphenyl phosphine and 0.55 g 3.2 mM, ethyl diazo carboxylate were added to 1 g of poly(propylene glycol) (average mol. Weight 424, n=7) in 60 ml dichloromethane. After stirring for 4 hours at room temperature, evaporation and chromatography gave 0.55 g viscous oil, a 73% yield. NMR CDCl₃ 7.30-6.9 (9H, m), 4.1-3.0 (m), 2.60 (2H, t, J=7.2 Hz), 1.2-1.1 (m). 0.1 g, 0.33 mmol of this product, potassium carbonate (0.069 g, 0.5 mmol, thinly crushed) and THF (3 mL, dried over KOH pellets) were put in a round-bottom flask equipped with a magnetic stirrer and a CaCl₂ drying tube. The mixture was cooled over an ice-salt bath (−10° C.) and a pre-cooled solution of di-tert-butyldicarbonate (0.066 g, 0.30 mmole) in 2 mL THF (dried) was introduced dropwise. The mixture was allowed to stir at ice temperature for 1 hour and then for 2 days at room temperature. The reaction mixture was then evaporated, water (5 mL) introduced and the product was extracted with two 10 mL portions of ethyl acetate. The combined extracts were dried over anhydrous magnesium sulfate, paper-filtered and the solvent removed. The oily residue was triturated with a small amount of n-hexane and the solid formed recovered by vacuum filtration (yield 0.12 g, 90.1%). Alternatively, the oily residue can be dissolved in an 1:1 mixture of ethyl acetate and hexane and the product recrystallised.

Synthesis 10: Compound 12
R=PPG; n=12; MW=996

Compound 12 was prepared as described in Synthesis 9 above for Compound 11 from 0.2 g Compound 10 to give a 0.3 g, 46% yield.

Synthesis 11: Compound 13
R=PPG; n=17; MW=1286

Compound 13 was prepared using the same procedure as described above in Synthesis 9 for Compound 11, with the substitution of the PPG, n=7 for PPG, n=17.

Compounds Synthesised from Compound 5

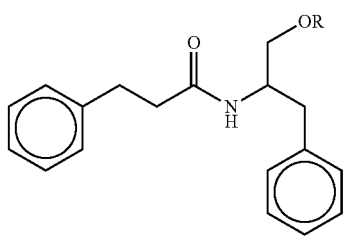
Formula B

Synthesis 12: Compound 14
R=PPG; n=7; MW=690

Compound 14 was prepared as described above in Synthesis 9 from 0.22 g Compound 5 to give a 0.25 g, 47% yield.

Synthesis 13: Compound 15
R=PPG; n=17; MW=1270

Compound 15 was prepared as above in Synthesis 9 from 0.2 g Compound 5 to give 0.33 g, 33% yield.

Compounds Synthesised from Compound 6 (Tyrosinol)

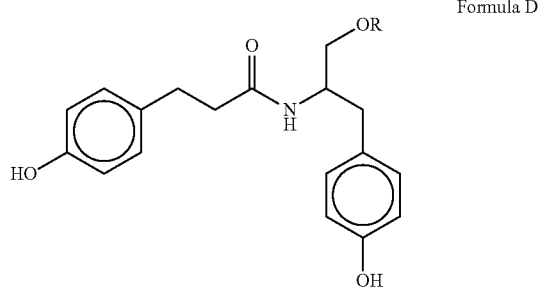

Formula D

Synthesis 14: Compound 16
R=PPG; n=7; MW=722

Compound 16 was prepared as described above in Synthesis 9 from 0.2 g Compound 6 to give a 0.21 g, 46% yield.

Synthesis 15: Compound 17
R=PPG; n=17; MW=1302

Compound 17 was prepared as described above in Synthesis 9 from 0.23 g Compound 6 to give a 0.28 g, 29% yield.

Compounds Synthesised from Compound 8

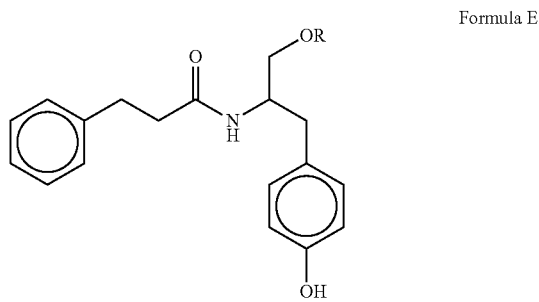

Formula E

Synthesis 16: Compound 18
R=PPG; n=7; MW=706

Mesylation of PPG 106 mg of $PPG_{425}$ (0.25 mmol) was reacted with 90 mole-percent of mesyl chloride (26 mg, 2 drops) and 0.4 mmol pyridine (31.6 mg, 2 drops) to afford the mono-mesylated PPG (A). After combining PPG, mesyl chloride and pyridine, the mesylation reaction was carried out at 0° C. over 30 minutes while stirring, and then the reaction was continued for another 60 minutes at room temperature. During mixing, the reaction mixture turned from colorless to milky-white. The mixture was then dissolved in 5 mL methylene chloride and the organic phase was washed twice with 1M HCl solution, then twice with 1M NaOH solution and once with water. The organic phase was dried over anhydrous sodium sulfate, filtered and the solvent removed.

Sodium Activation.

0.1 g of the above product (0.25 mmol) was dissolved in 5 mL of absolute ethanol and then reacted with an equimolar amount of sodium ethoxide in absolute ethanol (previously prepared by reacting 0.25 mg-atom of sodium with an access of absolute ethanol). The ethanol of the combined solutions was evaporated to total dryness to yield the sodium salt (B).

Reacting A and B

A was dissolved in 5 mL of a potassium hydroxide-dried acetonitrile and the solution introduced into a round-bottom flask containing a magnetic stirrer. 5 mL of dried acetonitrile solution of B was introduced into the flask, followed by a catalytic amount (few crystals) of potassium iodide. A reflux condenser and a gas bubbler adjusted on top of it were connected to the reaction vessel and the reaction mixture was allowed to reflux under nitrogen atmosphere, while stirring, for 24 hrs. The reaction mixture was then paper-filtered and the solvent removed. The residue was dissolved in 2 mL of ethyl acetate and then passed through a silica-gel column, using ethyl acetate for elution. The TLC (elution with ethyl acetate) UV-absorbing spot at $R_f$=0.55 turned out to contain the desired product 3 (a mixture of molecules containing different PPG sub-unit lengths), however, containing also some unreacted PPG. Other fractions contained unreacted mesylated PPG and doubly-mesylated PPG.

Synthesis 17: Compound 19
R=PPG; n=17; MW=1000

Compound 19 was prepared using the same procedure as described above in Synthesis 16 for Compound 18, with the substitution of the PPG, n=7 for PPG, n=17.

The following experiments were conducted to demonstrate the utility of compounds of the invention in the treatment of pain.

EXAMPLE 1

Hot-Plate Test of Balb/c Mice 21-week old male Balb/c mice (non-naive) were divided into four groups of approximately 7 or 8 mice per group and treated at t=0 minutes with Compound 18 intraperitoneally with 0.2 mL solution as detailed in Table 1 below:

TABLE 1

| Group | | |
|---|---|---|
| 1 | Control | 0.2 mL/mouse |
| | | (20 µL DMSO + 1980 µm saline) |
| 2 | 100 µg/mouse | 191 µL (10.5 mg Compound 18 + 200 µL |
| | Compound 18 | DMSO + 1800 µL saline) + 1809 µL saline |
| 3 | 1 µg/mouse | 20 µL (Compound 18 100 µg/mouse) + |
| | Compound 18 | 1980 µL saline |
| 4 | 0.01 µg/mouse | 20 µL (Compound 18 1 µg/mouse) + |
| | Compound 18 | 1980 µL saline |

The mice were tested using a hot-plate (J. P. Callaghan & S. G. Holtzman, "Quantification of the Analgesic Activity of Narcotic Antagonists by a Modified Hot-Plate Procedure", *J. Pharmacol. Exp. Ther.*, 1975; 192(3): 497-505) at t=−60 mins., 0 mins., 60 mins., 120 mins., 180 mins., 240 mins. and 300 mins. The results are set forth in Table 2 below and illustrated in FIG. 1 of the accompanying drawings. The numbers in the columns are time taken (in seconds) for the mice to react to the hot-plate. A licking of the fore or hind paws was used as the end-point for the determination of response latencies.

TABLE 2

| Group | # mouse | −60 | 0 | 60 | 120 | 180 | 240 | 300 |
|---|---|---|---|---|---|---|---|---|
| Control 10% DMSO | 1 | 25 | 18 | 27 | 28 | 24 | 20 | 24 |
| | 2 | 25 | 22 | 23 | 35 | 25 | 22 | 32 |
| | 3 | 33 | 20 | 31 | 24 | 24 | 23 | 20 |
| | 4 | 22 | 23 | 20 | 21 | 20 | 19 | 16 |
| | 5 | 21 | 22 | 21 | 25 | 24 | 28 | 23 |
| | 6 | 27 | 25 | 22 | 22 | 21 | 24 | 23 |
| | 7 | 26 | 24 | 23 | 22 | 15 | 20 | 24 |
| | 8 | 22 | 25 | 21 | 22 | 21 | 17 | 14 |
| | Average | 25.1 | 22.4 | 23.5 | 24.9 | 21.8 | 21.6 | 22.0 |
| | SD | 3.8 | 2.4 | 3.7 | 4.7 | 3.3 | 3.4 | 5.5 |
| | SE | 1.4 | 0.9 | 1.3 | 1.7 | 1.2 | 1.2 | 2.0 |
| 100 μg/mouse | 9 | 28 | 19 | 15 | 18 | 25 | 30 | 22 |
| | 10 | 21 | 26 | 24 | 19 | 26 | 32 | 28 |
| | 11 | 24 | 25 | 21 | 26 | 37 | 43 | 23 |
| | 12 | 23 | 22 | 24 | 24 | 29 | 41 | 35 |
| | 13 | 22 | 21 | 18 | 31 | 37 | 26 | 34 |
| | 14 | 21 | 15 | 23 | 30 | 41 | 36 | 29 |
| | 15 | 31 | 28 | 29 | 28 | 28 | 56 | 33 |
| | Average | 24.3 | 22.3 | 22.0 | 25.1 | 31.9 | 37.7 | 29.1 |
| | SD | 3.8 | 4.5 | 4.5 | 5.1 | 6.3 | 10.0 | 5.2 |
| | SE | 1.4 | 1.7 | 1.7 | 1.9 | 2.4 | 3.8 | 2.0 |
| t-test vs. Control | | 0.6786 | 0.9634 | 0.5011 | 0.9178 | 0.0045 | 0.0046 | 0.0232 |
| 1 μg/mouse | 16 | 27 | 13 | 29 | 26 | 35 | 19 | 17 |
| | 17 | 21 | 18 | 17 | 26 | 35 | 34 | 28 |
| | 18 | 19 | 24 | 19 | 34 | 36 | 42 | 41 |
| | 19 | 26 | 19 | 22 | 30 | 31 | 35 | 40 |
| | 20 | 22 | 22 | 19 | 33 | 38 | 42 | 24 |
| | 21 | 33 | 35 | 29 | 64 | 86 | 44 | 37 |
| | 22 | 22 | 24 | 21 | 27 | 28 | 47 | 18 |
| | Average | 24.3 | 22.1 | 22.3 | 34.3 | 41.3 | 37.6 | 29.3 |
| | SD | 4.8 | 6.9 | 4.9 | 13.5 | 20.0 | 9.4 | 10.2 |
| | SE | 1.8 | 2.6 | 1.8 | 5.1 | 7.6 | 3.6 | 3.8 |
| t-test vs. Control | | 0.7159 | 0.9346 | 0.6007 | 0.1212 | 0.0415 | 0.0034 | 0.1252 |
| 0.01 μg/mouse | 23 | 18 | 24 | 18 | 25 | 36 | 31 | 27 |
| | 24 | 26 | 21 | 13 | 11 | 22 | 34 | 26 |
| | 25 | 29 | 28 | 26 | 35 | 28 | 32 | 29 |
| | 26 | 19 | 22 | 34 | 36 | 24 | 22 | 24 |
| | 27 | 33 | 16 | 16 | 34 | 37 | 20 | 22 |
| | 28 | 24 | 35 | 26 | 21 | 36 | 27 | 17 |
| | 29 | 21 | 15 | 20 | 24 | 22 | 24 | 25 |
| | Average | 24.3 | 23.0 | 21.9 | 26.6 | 29.3 | 27.1 | 24.3 |
| | SD | 5.5 | 6.9 | 7.2 | 9.1 | 6.9 | 5.4 | 3.9 |
| | SE | 2.1 | 2.6 | 2.7 | 3.4 | 2.6 | 2.0 | 1.5 |
| t-test vs. Control | | 0.7408 | 0.8269 | 0.6010 | 0.6677 | 0.0287 | 0.0417 | 0.3683 |

As those skilled in the art will recognise, these data show that Compound 18 according to the invention shows analgesic activity in mice.

EXAMPLE 2

Hot-Plate Test of Balb/c Mice vs. Imipramine (i.p. & p.o.)

14-week old male Balb/c mice (non-naive) were divided into four groups of seven mice per group and treated at t=0 as detailed in Table 3 below:

TABLE 3

| Group | | |
|---|---|---|
| 1 | Control | i.p.: 0.3 mL/mouse (20 μL DMSO + 2680 μL saline) |
| | | p.o.: 0.3 mL/mouse (20 μL DMSO + 2680 μL saline) |
| 2 | 5 mg/kg Imipramine | i.p.: 5 mg/kg (1.35 mg imipramine + 2.7 mL saline) |
| | | p.o.: 0.3 mL/mouse (20 μL DMSO + 2680 μL saline) |
| 3 | 0.5 mg/mouse Compound 18 (i.p.) | i.p.: 0.3 mL/mouse (0.479 mL Compound 18 stock + 2.221 mL saline) |
| | | p.o.: 0.3 mL/mouse (20 μL DMSO plus 2680 μL saline) |

TABLE 3-continued

| Group | | |
|---|---|---|
| 4 | 0.5 mg/mouse Compound 18 (p.o.) | i.p.: 0.3 mL/mouse (20 μL DMSO plus 2680 μL saline) p.o.: 0.3 mL/mouse (0.479 mL Compound 18 stock + 2.221 mL saline) |

Compound 18 stock comprises 9.4 mg Compound 18, 0.2 mL DMSO and 0.8 mL saline.

Figure 2:
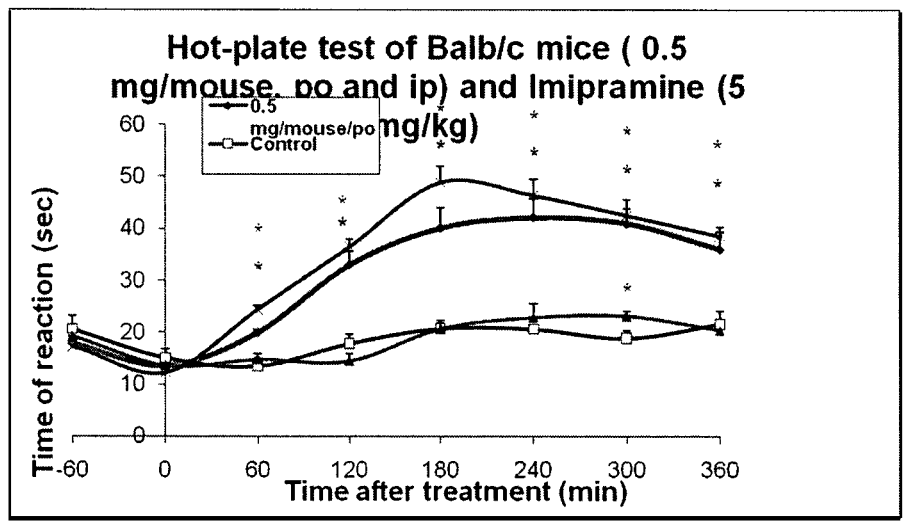
FIG. 2 is a graph showing the results of a Hot-Plate Test using Balb/c mice following administration of Compound 18 of the invention or imipramine.

As in Example 1 above, the response latencies of the mice in the respective groups were tested using a hot-plate at t=−60 mins., 0 mins., 60 mins., 120 mins., 180 mins., 240 mins., 300 mins. and 360 mins. The results are set forth in Table 4 below and are illustrated in FIG. 2 of the drawings.

TABLE 4

| Group | # mouse | weight | −60 | 0 | 60 | 120 | 180 | 240 | 300 | 360 |
|---|---|---|---|---|---|---|---|---|---|---|
|  | 1 | 24.3 | 19 | 16 | 19 | 32 | 30 | 31 | 32 | 25 |
|  | 2 | 23.5 | 12 | 8 | 18 | 23 | 25 | 29 | 34 | 27 |
| A | 3 | 21.5 | 17 | 15 | 21 | 41 | 49 | 54 | 42 | 36 |
| 0.5 mg/mouse/p.o. | 4 | 20.9 | 19 | 7 | 20 | 26 | 40 | 42 | 38 | 35 |
|  | 5 | 21.2 | 16 | 14 | 22 | 38 | 37 | 47 | 56 | 47 |
|  | 6 | 25.6 | 25 | 18 | 22 | 42 | 44 | 37 | 41 | 50 |
| n = 7 | 7 | 25.6 | 17 | 17 | 18 | 29 | 56 | 55 | 44 | 32 |
|  | Average | 23.2 | 17.9 | 13.6 | 20.0 | 33.0 | 40.1 | 42.1 | 41.0 | 36.0 |
|  | SD | 2.0 | 3.9 | 4.4 | 1.7 | 7.5 | 10.7 | 10.4 | 7.9 | 9.5 |
|  | SE | 0.7 | 1.4 | 1.5 | 0.6 | 2.6 | 3.8 | 3.7 | 2.8 | 3.3 |
| t-test vs. Control |  |  | 0.3832 | 0.5115 | 0.0027 | 0.0011 | 0.0025 | 0.0014 | 0.0001 | 0.0072 |
|  | 8 | 24.3 | 20 | 18 | 10 | 14 | 18 | 22 | 24 | 25 |
| Control | 9 | 24.5 | 22 | 16 | 11 | 21 | 24 | 23 | 21 | 21 |
| B | 10 | 24.8 | 32 | 23 | 12 | 18 | 17 | 21 | 14 | 12 |
|  | 11 | 21.7 | 25 | 10 | 10 | 12 | 22 | 17 | 17 | 25 |
|  | 12 | 24 | 11 | 12 | 19 | 23 | 24 | 20 | 18 | 13 |
|  | 13 | 25 | 19 | 13 | 16 | 24 | 21 | 21 | 15 | 26 |
| n = 7 | 14 | 23.2 | 15 | 14 | 17 | 13 | 19 | 20 | 23 | 29 |
|  | Average | 23.9 | 20.6 | 15.1 | 13.6 | 17.9 | 20.7 | 20.6 | 18.9 | 21.6 |
|  | SD | 1.1 | 6.8 | 4.3 | 3.7 | 4.9 | 2.8 | 1.9 | 3.9 | 6.6 |
|  | SE | 0.4 | 2.6 | 1.6 | 1.4 | 1.9 | 1.1 | 0.7 | 1.5 | 2.5 |
|  | 15 | 25.5 | 21 | 13 | 14 | 19 | 20 | 21 | 22 | 25 |
|  | 16 | 24.1 | 15 | 14 | 16 | 16 | 18 | 16 | 25 | 18 |
| C | 17 | 23.5 | 26 | 16 | 16 | 12 | 14 | 19 | 21 | 16 |
|  | 18 | 22.6 | 24 | 15 | 16 | 10 | 19 | 16 | 25 | 30 |
| Imipramine 5 mg/kg | 19 | 22.9 | 19 | 12 | 20 | 20 | 22 | 31 | 21 | 18 |
|  | 20 | 21.5 | 17 | 14 | 10 | 14 | 24 | 22 | 21 | 20 |
| n = 7 | 21 | 22.9 | 13 | 12 | 12 | 11 | 28 | 35 | 27 | 16 |
|  | Average | 23.3 | 19.3 | 13.7 | 14.9 | 14.6 | 20.7 | 22.9 | 23.1 | 20.4 |
|  | SD | 1.3 | 4.7 | 1.5 | 3.2 | 3.9 | 4.5 | 7.4 | 2.5 | 5.2 |
|  | SE | 0.4 | 1.7 | 0.5 | 1.1 | 1.4 | 1.6 | 2.6 | 0.9 | 1.8 |
| t-test vs. Control |  |  | 0.6892 | 0.4357 | 0.5017 | 0.1945 | 1.0000 | 0.4543 | 0.0334 | 0.7267 |
|  | 22 | 21 | 28 | 14 | 21 | 33 | 35 | 38 | 37 | 34 |
| 0.5 mg/mouse/i.p. | 23 | 23.2 | 19 | 15 | 26 | 29 | 56 | 70 | 57 | 38 |
|  | 24 | 23.9 | 9 | 11 | 21 | 37 | 38 | 37 | 28 | 33 |
| D | 25 | 24.2 | 14 | 8 | 28 | 44 | 67 | 44 | 58 | 38 |
|  | 26 | 23.2 | 16 | 12 | 23 | 43 | 52 | 44 | 40 | 35 |
|  | 27 | 22.5 | 23 | 16 | 27 | 33 | 49 | 48 | 41 | 51 |
| n = 7 | 28 | 26.5 | 12 | 10 | 25 | 36 | 45 | 43 | 36 | 40 |
|  | Average | 23.5 | 17.3 | 12.3 | 24.4 | 36.4 | 48.9 | 46.3 | 42.4 | 38.4 |
|  | SD | 1.7 | 6.6 | 2.9 | 2.8 | 5.5 | 10.9 | 11.1 | 11.1 | 6.1 |
|  | SE | 0.5 | 1.9 | 0.8 | 0.8 | 1.6 | 3.2 | 3.2 | 3.2 | 1.8 |
| t-test vs. Control |  |  | 0.3763 | 0.1756 | 0.0001 | 0.0000 | 0.0003 | 0.0008 | 0.0009 | 0.0003 |

Compound 18 thus showed analgesic activity, not only against negative control, but also against imipramine (p<0.0000) as a positive control.

Further, the results of Example 2 also show that Compound 18 manifested activity by the oral route at almost the same level of magnitude as via intraperitoneal injection.

EXAMPLE 3

Oedema Test

The ability of the compounds of the invention to treat inflammation was tested using the carrageenan-induced paw oedema test in rats (see, e.g., P. G. Winyard & D. A. Willoughby, "Inflammation Protocols", *Methods in Molecular Biology*, 2003; Vol. 225).

21-week-old male Sprague-Dawley (SD) rats (non-naive) were divided into four groups of seven rats per group untreated at t=−2 hr as detailed in Table 5 below:

TABLE 5

| Group | | |
|---|---|---|
| 1 | Control | |
| 2 | 0.1 μg/0.4 mL/rat Compound 18 | 32 μL (Compound 18 10 μg/0.4 mL/rat) + 3168 μL saline |
| 3 | 10 μg/0.4 mL/rat Compound 18 | 32 μL (Compound 18 1 mg/0.4 mL/rat) + 3168 μL saline |
| 4 | 1 mg/0.4 mL/rat Compound 18 | Compound 18 stock solution (8.9 mg + 178 μL DMSO + 712 μL saline = 8.9 mg/890 μL) |

At t=0 (i.e., 2 hours after administration of the control/Compound 18 formulations) paw oedema was induced by injecting 200 μL of a 1% (60 mg+6000 μL) solution of λ-carrageenan in normal saline into the plantar surface of the left hind paw of the rats. The area and the height of the induced oedema was measured at t=4, 24 and 48 hours after injection using a caliper. The anti-inflammatory activity of the injected Compound 18 formulation was expressed as the amount of reduction relative to the control in the height and volume of the oedema, the volume being calculated as the product of the oedema measured height and area.

The results are set forth in Tables 6 to 9 below and are illustrated graphically in FIGS. 3 and 4 of the accompanying drawings. Table 6 gives the data for the measured oedema heights (in mm), and Table 7 and FIG. 3 give the corresponding average figures for each group of rats.

Figures 3, 4:
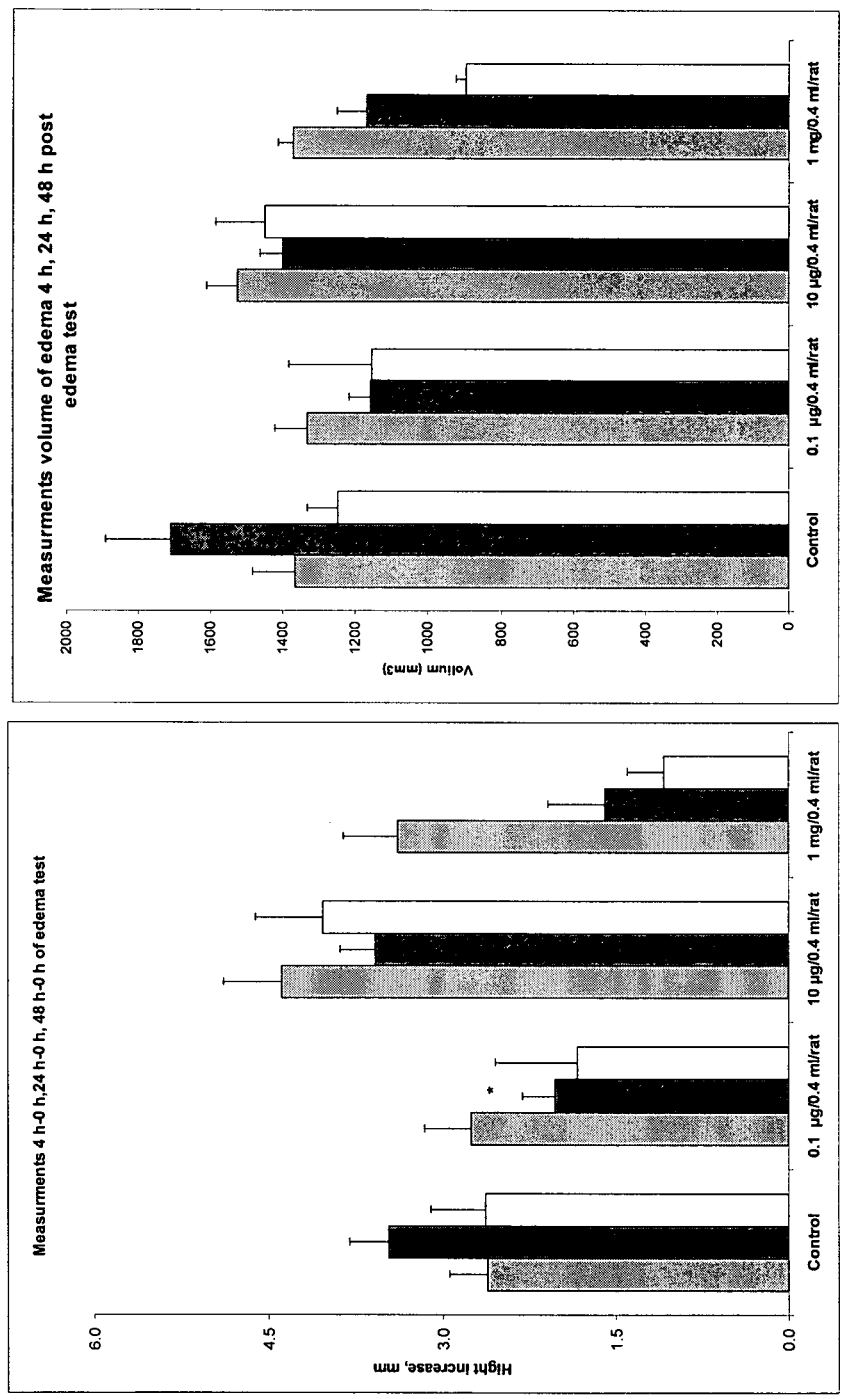
FIG. 3 is a histogram showing the reduction in the height of carrageenan-induced oedemas in SD rats following administration of Compound 18 of the invention.
FIG. 4 is a histogram showing the reduction in the volume of carrageenan-induced oedemas in SD rats following administration Compound 18 of the invention.

Table 8 gives the data for the measured oedema volumes (in $mm^3$) and Table 9 and FIG. 4 give the corresponding average figures for each group of rats.

TABLE 7

Average Reduction in Oedema Height with Time

| | 4 h/mm | 24 h/mm | 48 h/mm |
|---|---|---|---|
| Control | 2.6 | 3.5 | 2.6 |
| 0.1 μg/0.4 ml/rat | 2.8 | 2.0 | 1.8 |
| 10 μg/0.4 ml/rat | 4.4 | 3.6 | 4.0 |
| 1 mg/0.4 ml/rat | 3.4 | 1.6 | 1.1 |

TABLE 9

Average Reduction in Oedema Volume with Time

| | 4 h/$mm^3$ | 24 h/$mm^3$ | 48 h/$mm^3$ |
|---|---|---|---|
| Control | 1366.2 | 1711.6 | 1249.2 |
| 0.1 μg/0.4 ml/rat | 1334.4 | 1158.3 | 1154.9 |
| 10 μg/0.4 ml/rat | 1527.0 | 1400.2 | 1451.3 |
| 1 mg/0.4 ml/rat | 1371.7 | 1171.1 | 897.5 |

These data confirm the anti-inflammatory properties of Compound 18.

TABLE 6

| Group | # rat | H 0 h | H 4 h | H 24 h | H 48 h | H 4 h – H 0 h | H 24 h – H 0 h | H 48 h – H 0 h |
|---|---|---|---|---|---|---|---|---|
| | 1 | 5.15 | 6.65 | 7.4 | 6.36 | 1.5 | 2.25 | 1.2 |
| | 2 | 3.69 | 5.55 | 7.58 | 5.72 | 1.86 | 3.89 | 2.0 |
| | 3 | 3.73 | 5.93 | 6.61 | 5.76 | 2.2 | 2.88 | 2.0 |
| Control | 4 | 3.4 | 6.85 | 7.77 | 8.05 | 3.45 | 4.37 | 4.7 |
| 5% DMSO | 5 | 3.7 | 6.8 | 8.09 | 7.71 | 3.1 | 4.39 | 4.0 |
| | 6 | 3.6 | 7.4 | 7.5 | 6.27 | 3.8 | 3.9 | 2.7 |
| | 7 | 4.2 | 6.6 | 6.78 | 6.04 | 2.4 | 2.58 | 1.8 |
| | Average | 3.9 | 6.5 | 7.4 | 6.6 | 2.6 | 3.5 | 2.6 |
| | SD | 0.6 | 0.6 | 0.5 | 0.9 | 0.9 | 0.9 | 1.2 |
| | SE | 0.2 | 0.2 | 0.2 | 0.4 | 0.3 | 0.3 | 0.5 |
| | 8 | 4.4 | 6.05 | 6.02 | 6.1 | 1.65 | 1.62 | 1.7 |
| | 9 | 5.5 | 9.03 | 8.18 | 6.57 | 3.53 | 2.68 | 1.1 |
| | 10 | 5.56 | 6.6 | 6.57 | 4.81 | 1.04 | 1.01 | −0.8 |
| 0.1 μg/0.4 ml/rat | 11 | 4.6 | 7.5 | 5.86 | 5.87 | 2.9 | 1.26 | 1.3 |
| | 12 | 4.5 | 8.3 | 7.35 | 9.98 | 3.8 | 2.85 | 5.5 |
| | 13 | 3.6 | 6.4 | 6.13 | 5.48 | 2.8 | 2.53 | 1.9 |
| | 14 | 4.9 | 8.5 | 7.19 | 7.1 | 3.6 | 2.29 | 2.2 |
| | Average | 4.7 | 7.5 | 6.8 | 6.6 | 2.8 | 2.0 | 1.8 |
| | SD | 0.7 | 1.2 | 0.9 | 1.7 | 1.0 | 0.7 | 1.9 |
| | SE | 0.3 | 0.4 | 0.3 | 0.6 | 0.4 | 0.3 | 0.7 |
| t-test vs. Control | | 0.0374 | 0.0899 | 0.1251 | 1.0000 | 0.7826 | 0.0065 | 0.3689 |
| | 15 | 4.5 | 7.6 | 8.43 | 7.14 | 3.1 | 3.93 | 2.6 |
| | 16 | 3.4 | 10.2 | 8.17 | 10.7 | 6.8 | 4.77 | 7.3 |
| | 17 | 3.6 | 8.07 | 6.18 | 8.02 | 4.47 | 2.58 | 4.4 |
| 10 μg/0.4 ml/rat | 18 | 3.68 | 8.26 | 7 | 7.4 | 4.58 | 3.32 | 3.7 |
| | 19 | 4.63 | 7.42 | 7.26 | 7.66 | 2.79 | 2.63 | 3.0 |
| | 20 | 3.98 | 8.9 | 7.59 | 7.49 | 4.92 | 3.61 | 3.5 |
| | 21 | 3.99 | 8.04 | 8.2 | 7.56 | 4.05 | 4.21 | 3.6 |
| | Average | 4.0 | 8.4 | 7.5 | 8.0 | 4.4 | 3.6 | 4.0 |
| | SD | 0.5 | 0.9 | 0.8 | 1.2 | 1.3 | 0.8 | 1.5 |
| | SE | 0.2 | 0.4 | 0.3 | 0.5 | 0.5 | 0.3 | 0.6 |
| t-test vs. Control | | 0.8784 | 0.0015 | 0.6733 | 0.0308 | 0.0134 | 0.8068 | 0.0896 |
| | 22 | 4.92 | 7.6 | 6.39 | 6.06 | 2.68 | 1.47 | 1.1 |
| | 23 | 4.9 | 7.8 | 6.84 | 6 | 2.9 | 1.94 | 1.1 |
| | 24 | 5.45 | 7.6 | 5.07 | 5.6 | 2.15 | −0.38 | 0.1 |

TABLE 6-continued

| Group | # rat | H 0 h | H 4 h | H 24 h | H 48 h | H 4 h − H 0 h | H 24 h − H 0 h | H 48 h − H 0 h |
|---|---|---|---|---|---|---|---|---|
| 1 mg/0.4 ml/rat | 25 | 4.9 | 8.6 | 7.59 | 6.55 | 3.7 | 2.69 | 1.7 |
| | 26 | 3.7 | 9.57 | 7.29 | 6.32 | 5.87 | 3.59 | 2.6 |
| | 27 | 4.8 | 8.46 | 6.19 | 5.37 | 3.66 | 1.39 | 0.6 |
| | 28 | 5.66 | 8.4 | 6.15 | 6.05 | 2.74 | 0.49 | 0.4 |
| | Average | 4.9 | 8.3 | 6.5 | 6.0 | 3.4 | 1.6 | 1.1 |
| | SD | 0.6 | 0.7 | 0.8 | 0.4 | 1.2 | 1.3 | 0.8 |
| | SE | 0.2 | 0.3 | 0.3 | 0.2 | 0.5 | 0.5 | 0.3 |
| t-test vs. Control | | | 0.0108 | 0.0004 | 0.0388 | 0.1801 | 0.2007 | 0.0105 | 0.0209 |

TABLE 8

| Group | # rat | V 4 h | V 24 h | V 48 h | V 24 h − V 4 h | V48 h − V4 h |
|---|---|---|---|---|---|---|
| | 1 | 1277.2 | 2645.4 | 1316.2 | 1368.2 | 39.0 |
| | 2 | 988.4 | 1776.3 | 1159.6 | 787.9 | 171.2 |
| | 3 | 1229.7 | 1296.3 | 1104.6 | 66.6 | −125.1 |
| Control | 4 | 1556.0 | 1790.4 | 1588.0 | 234.4 | 32.1 |
| 5% DMSO | 5 | 1841.5 | 1816.8 | 1484.2 | −24.8 | −357.3 |
| | 6 | 1627.4 | 1347.0 | 1017.5 | −280.4 | −609.9 |
| | 7 | 1043.0 | 1309.2 | 1074.1 | 266.2 | 31.1 |
| | Average | 1366.2 | 1711.6 | 1249.2 | 345.5 | −117.0 |
| | SD | 317.3 | 476.2 | 219.0 | 557.8 | 274.6 |
| | SE | 119.9 | 180.0 | 82.8 | 210.8 | 103.8 |
| | 8 | 1343.9 | 1064.9 | 968.3 | −279.0 | −375.6 |
| | 9 | 1686.4 | 1263.4 | 979.1 | −422.9 | −707.3 |
| | 10 | 985.4 | 1189.3 | 637.8 | 203.9 | −347.5 |
| 0.1 µg/0.4 ml/rat | 11 | 1212.5 | 927.6 | 820.7 | −284.9 | −391.8 |
| | 12 | 1456.5 | 1354.7 | 2394.0 | −101.8 | 937.5 |
| | 13 | 1160.8 | 1029.1 | 810.8 | −131.7 | −350.0 |
| | 14 | 1495.3 | 1279.2 | 1473.6 | −216.1 | −21.7 |
| | Average | 1334.4 | 1158.3 | 1154.9 | −176.1 | −179.5 |
| | SD | 235.1 | 154.8 | 605.6 | 198.7 | 531.0 |
| | SE | 88.8 | 58.5 | 228.9 | 75.1 | 200.7 |
| t-test vs. Control | | 0.8352 | 0.0214 | 0.7092 | 0.0502 | 0.7884 |
| | 15 | 1113.1 | 1403.9 | 1157.6 | 290.8 | 44.5 |
| | 16 | 1689.2 | 1450.0 | 2222.9 | −239.2 | 533.7 |
| | 17 | 1622.1 | 1117.3 | 1388.0 | −504.8 | −234.1 |
| 10 µg/0.4 ml/rat | 18 | 1486.4 | 1355.2 | 1404.7 | −131.2 | −81.6 |
| | 19 | 1396.5 | 1295.4 | 1391.4 | −101.1 | −5.1 |
| | 20 | 1792.1 | 1493.4 | 1389.7 | −298.7 | −402.4 |
| | 21 | 1589.9 | 1686.1 | 1205.0 | 96.2 | −384.9 |
| | Average | 1527.0 | 1400.2 | 1451.3 | −126.9 | −75.7 |
| | SD | 223.4 | 176.1 | 354.9 | 261.4 | 321.0 |
| | SE | 84.5 | 66.5 | 134.2 | 98.8 | 121.3 |
| t-test vs. Control | | 0.2966 | 0.1452 | 0.2286 | 0.0749 | 0.8003 |
| | 22 | 1369.9 | 1154.3 | 824.5 | −215.6 | −545.4 |
| | 23 | 1241.3 | 1256.1 | 839.9 | 14.8 | −401.4 |
| | 24 | 1246.3 | 885.4 | 947.9 | −360.9 | −298.4 |
| 1 mg/0.4 ml/rat | 25 | 1508.5 | 1408.3 | 962.3 | −100.2 | −546.2 |
| | 26 | 1382.2 | 1411.4 | 971.2 | 29.2 | −411.0 |
| | 27 | 1523.3 | 1157.6 | 802.7 | −365.8 | −720.7 |
| | 28 | 1330.6 | 924.5 | 934.3 | −406.1 | −396.2 |
| | Average | 1371.7 | 1171.1 | 897.5 | −200.6 | −474.2 |
| | SD | 112.7 | 209.8 | 72.1 | 184.7 | 139.8 |
| | SE | 42.6 | 79.3 | 27.2 | 69.8 | 52.8 |
| t-test vs. Control | | 0.9664 | 0.0244 | 0.0046 | 0.0422 | 0.0136 |

EXAMPLE 4

Formalin Test 27-week old Balb/c mice (non-naive) were divided into four groups of 5 mice per group and treated at t=0 mins. with intraperitoneal control or Compound 18 solution as set forth in Table 10 below.

TABLE 10

| Group | | | |
|---|---|---|---|
| 1 | Control | 0.2 mL/mouse i.p. (0.2 mL DMSO + 3.52 mL saline) | |
| 2 | 0.02 mg/0.2 mL/mouse Compound 18 | 0.04 mL (Compound 18 0.5 mg/0.2 mL/mouse) + 0.96 mL saline | |
| 3 | 0.1 mg/0.2 mL/mouse Compound 18 | 0.2 mL (Compound 18 0.5 mg/0.2 mL/mouse) + 0.8 mL saline | |
| 4 | 0.5 mg/0.2 mL/mouse Compound 18 | Compound 18 9.3 mg + 0.2 mL DMSO + 3.5 mL saline | |

Following the method of S. Hunscaar & K. Hole, "The Formalin Test in Mice: Dissociation between Inflammatory and Non-Inflammatory Pain", *Pain,* 1987; 30:103-104, 20 µL of formalin 1% was injected via the intraplantar route subcutaneously into the right hind paw of each mouse 3 hours after administration of the control/Compound 18 solution. The mice were then returned to a glass chamber, and the formalin-induced flinching behaviour of the injected paw was counted.

Figure 5:
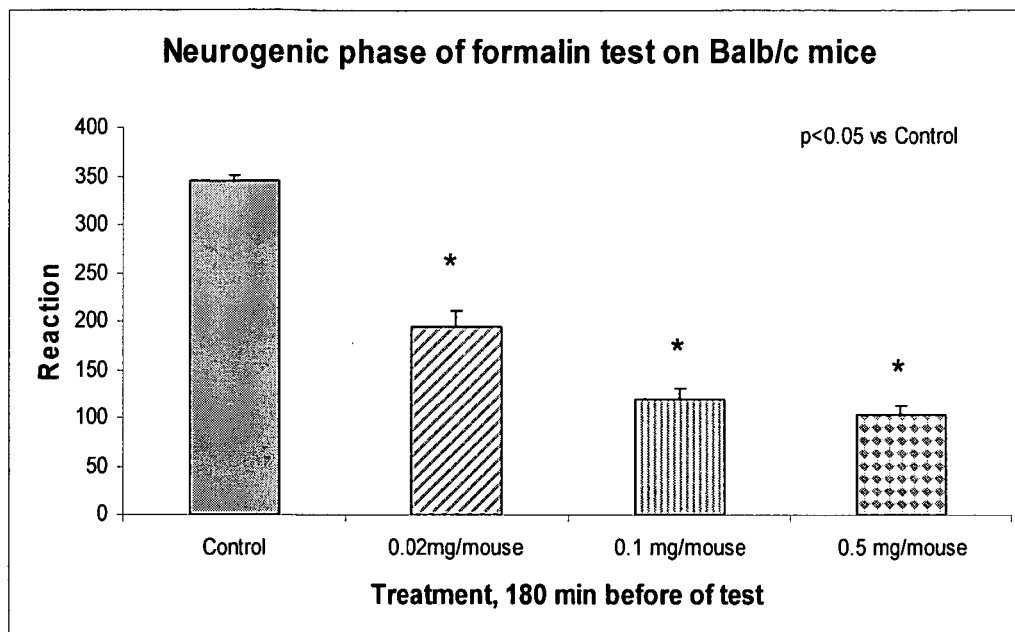
FIG. 5 is a histogram showing the number of paw licks of Balb/c mice during a first neurogenic phase following intraplanar injection of 1% formalin ("Formalin test")
Figure 6:
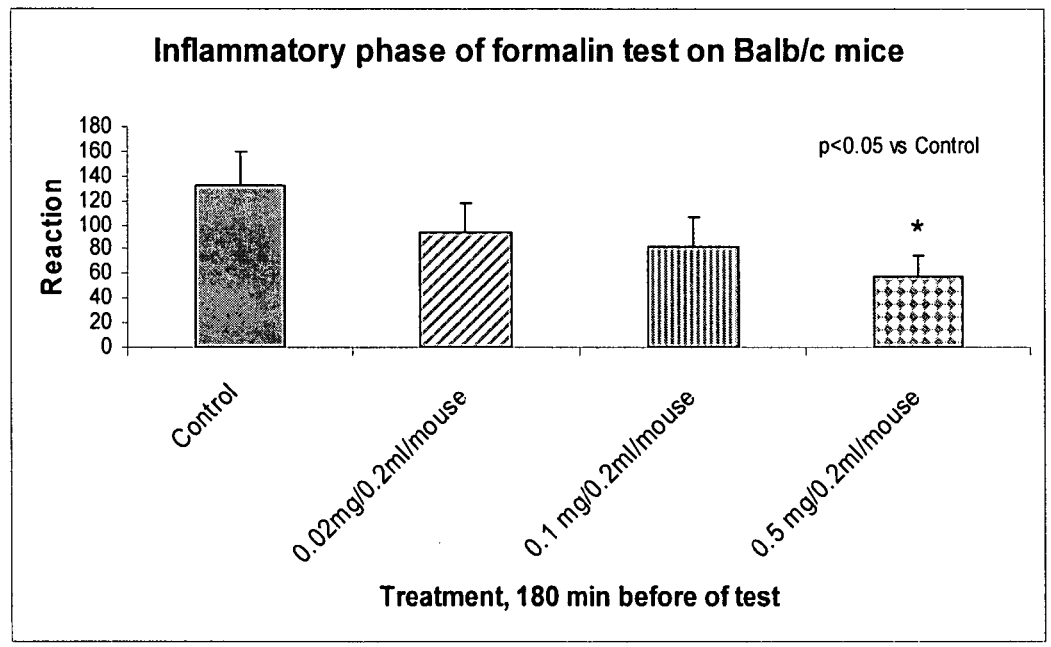
FIG. 6 is a histogram showing the number of paw licks of Balb/c mice during a second inflammation phase following intraplanar injection of 1% formalin.

Formalin-induced pain is biphasic; the amount of the paw-licking was determined during a first neurogenic phase (0-5 mins.) and subsequently during a second inflammatory phase (20-30 mins.) after formalin injection. The results are set forth in Table 11 below and illustrated graphically in FIGS. 5 and 6 of the drawings.

TABLE 11

| Group | # mouse | weight | treatment | formalin | 5 min | inflam. | 10 min |
|---|---|---|---|---|---|---|---|
|  | 1 | 27.8 | 08:20 | 11:20 | 342 | 11:40 | 62 |
|  | 2 | 30.8 | 08:30 | 11:30 | 348 | 11:50 | 116 |
| Control | 3 | 25.5 | 08:40 | 11:40 | 346 | 12:00 | 119 |
|  | 4 | 27.8 | 08:50 | 11:50 | 363 | 12:10 | 229 |
| 5 mice | 5 | 28 | 09:00 | 12:00 | 329 | 12:20 | 138 |
| Average |  | 28.0 |  |  | 345.6 |  | 132.8 |
| SD |  | 1.9 |  |  | 12.2 |  | 60.8 |
| SE |  | 0.8 |  |  | 5.5 |  | 27.2 |
|  | 6 | 27.3 | 09:10 | 12:10 | 161 | 12:30 | 87 |
|  | 7 | 26.6 | 09:20 | 12:20 | 189 | 12:40 | 120 |
| 0.02 mg/0.2 ml/mouse | 8 | 25.7 | 09:30 | 12:30 | 166 | 12:50 | 25 |
|  | 9 | 28.8 | 09:40 | 12:40 | 246 | 13:00 | 170 |
| 5 mice | 10 | 28.2 | 09:50 | 12:50 | 214 | 13:10 | 67 |
| Average |  | 27.3 |  |  | 195.2 |  | 93.8 |
| SD |  | 1.2 |  |  | 35.3 |  | 54.8 |
| SE |  | 0.6 |  |  | 15.8 |  | 24.5 |
| t-test vs. Control |  | 0.533363 |  |  | 0.000301 |  | 0.317755 |
|  | 11 | 26.9 | 10:50 | 13:50 | 86 | 14:10 | 64 |
|  | 12 | 29.2 | 11:00 | 14:00 | 117 | 14:20 | 13 |
| 0.1 mg/0.2 ml/mouse | 13 | 28.5 | 11:10 | 14:10 | 146 | 14:30 | 59 |
|  | 14 | 29.3 | 11:20 | 14:20 | 115 | 14:40 | 116 |
| 5 mice | 15 | 29.5 | 11:30 | 14:30 | 140 | 14:50 | 157 |
| Average |  | 28.7 |  |  | 120.8 |  | 81.8 |
| SD |  | 1.1 |  |  | 23.8 |  | 55.7 |
| SE |  | 0.5 |  |  | 10.6 |  | 24.9 |
| t-test vs. Control |  | 0.4950 |  |  | 0.0000 |  | 0.2040 |
|  | 16 | 28.5 | 11:40 | 14:40 | 99 | 15:00 | 101 |
|  | 17 | 30.7 | 11:50 | 14:50 | 131 | 15:10 | 55 |
| 0.5 mg/0.2 ml/mouse | 18 | 28.8 | 12:00 | 15:00 | 116 | 15:20 | 93 |
|  | 19 | 26.3 | 12:10 | 15:10 | 84 | 15:30 | 12 |
| 5 mice | 20 | 26.4 | 12:20 | 15:20 | 86 | 15:40 | 24 |
| Average |  | 28.1 |  |  | 103.2 |  | 57.0 |
| SD |  | 1.8 |  |  | 20.1 |  | 39.8 |
| SE |  | 0.8 |  |  | 9.0 |  | 17.8 |
| t-test vs. Control |  | 0.8952 |  |  | 0.0000 |  | 0.0529 |

These data further confirm the anti-inflammatory properties of Compound 18.

EXAMPLE 5
Open Field ("OF") Test 24 six-week old male BALB/c mice were divided into three groups of 8 mice per group and were treated at t=−90 mins. as set forth in Table 12 below.

TABLE 12

| Group | | |
|---|---|---|
| 1 | Control | 0.2 mL/mouse i.p. (20 μL DMSO + 980 μL saline) |

TABLE 12-continued

| Group | | |
|---|---|---|
| 2 | 0.1 mg/0.1 mL/mouse Compound 18 | 0.1 mL/mouse (0.111 mL Compound 18 stock solution + 0.889 mL saline) |
| 3 | 0.5 mg/0.1 mL/mouse Compound 18 | 0.1 mL/mouse (0.555 mL (Compound 18 stock solution 9.0 mg + 0.2 mL DMSO + 0.80 mL saline) + 0.445 mL saline) |

The mice were then subjected to an Open Field test for 60 minutes in four arenas, with the mice distributed as follows:

TABLE 13

|  | Arena 1 | Arena 2 | Arena 3 | Arena 4 | Treatment time | OF start time | OF finish time |
|---|---|---|---|---|---|---|---|
| 1 | Control | 0.1 mg | 0.5 mg | Control | 08:00 | 09:30 | 10:30 |
| 2 | 0.1 mg | 0.5 mg | Control | 0.1 mg | 09:05 | 10:35 | 11:35 |
| 3 | 0.5 mg | Control | 0.1 mg | 0.5 mg | 10:10 | 11:40 | 12:40 |

TABLE 13-continued

|   | Arena 1 | Arena 2 | Arena 3 | Arena 4 | Treatment time | OF start time | OF finish time |
|---|---------|---------|---------|---------|----------------|---------------|----------------|
| 4 | Control | 0.1 mg  | 0.5 mg  | Control | 11:15          | 12:45         | 13:45          |
| 5 | 0.1 mg  | 0.5 mg  | Control | 0.1 mg  | 12:20          | 13:50         | 14:50          |
| 6 | 0.5 mg  | Control | 0.1 mg  | 0.5 mg  | 13:25          | 14:55         | 15:55          |

An Open Field test measures activity in a novel environment and can be used to assess a combination of locomotor activity, exploratory drive, neophobia, agoraphobia and other aspects of anxiety or fear in mice, as well as motor function. The apparatus consists of a Perspex arena (approximately 44 cm×44 cm×50 cm high).

The activity of the mice was assessed by an EthoVision video track system (Noldus Ltd.) A centre zone ("zone 3"; approximately 16% of the total area), a border area ("zone 1"; an 8 cm wide border around the edge of the arena) and an intermediate zone ("zone 2"; the remaining area) were defined. Quantitative parameters, such as the distance travelled and average speed, were recorded for the centre zone and the entire arena.

The distance moved, mean velocity, total duration of immobility, total duration of strong mobility, mean turn angle, angular velocity, total duration of moving, total duration of not moving, in zone frequency for "zone 3", rearing frequency, in zone duration for "zone 3", in zone frequency for "zones 2+3", distance moved and in zone duration for "zones 2+3" are illustrated graphically in FIGS. 7A to 7N of the accompanying drawings respectively.

The results indicate that Compound 18 has no activity on the central nervous system.

The invention claimed is:

1. A method for treating or preventing nociceptive pain selected from somatic pain, visceral pain, and myofascial pain in a human or non-human animal patient in need thereof, which method comprises administering to said patient a therapeutic effective amount of at least one compound represented by formula I:

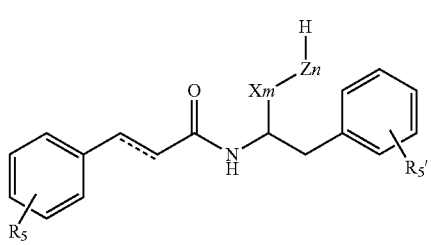

(I)

or a pharmaceutically acceptable salt thereof in which:
==== represents a single or a double bond; and $R_5$ and $R_5'$ are independently —H, —OH or —OR$_6$, where $R_6$ is a linear or branched $C_1$-$C_4$ alkyl; X is —O—, —CH$_2$O—, —CH$_2$CH$_2$O—, —CH(CH$_3$)CH$_2$O— or —CH$_2$CH(CH$_3$)O—; Z is —CH$_2$CH$_2$O—, —CH(CH$_3$)CH$_2$O— or —CH$_2$CH(CH$_3$)O—; m is an integer of 0 or 1; and n is 1-50.

2. The method of claim 1 for the treatment of acute or chronic nociceptive pain.

3. The method of claim 1 for the treatment of headache.

4. The method of claim 1, wherein m is 1.

5. The method of claim 1, wherein X is —CH$_2$O—.

6. The method of claim 4, wherein said compound is represented by formula III:

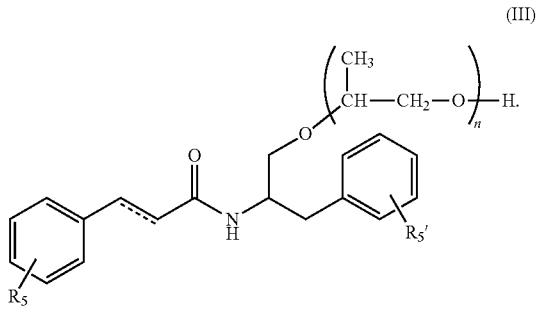

(III)

7. The method of claim 1, wherein $R_5$ is H or OH.
8. The method of claim 1, wherein $R_5'$ is H or OH.
9. The method of claim 1, wherein the compound is represented by formula IV, V, VI or VII:

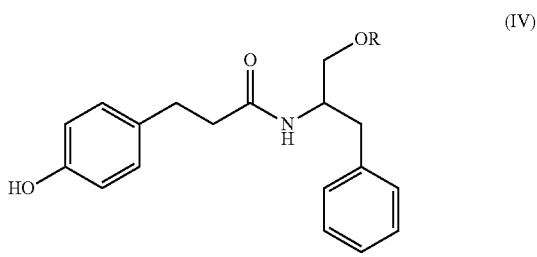

(IV)

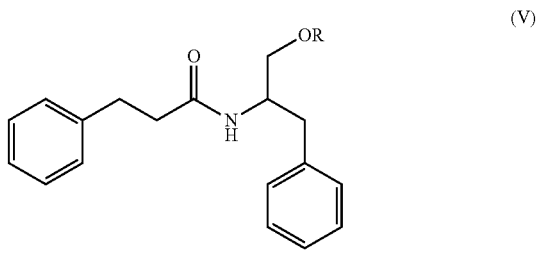

(V)

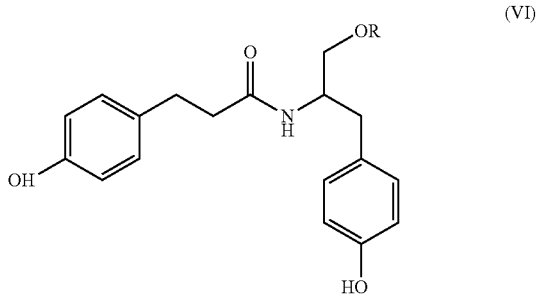

(VI)

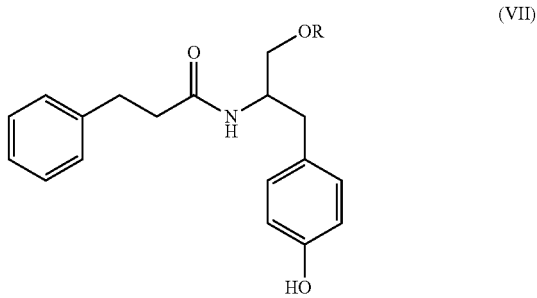

(VII)

in which R is a polyalkylene glycol polymer having n units, wherein n is an integer of 1-50.

10. The method of claim 1 comprising administering as a pharmaceutical composition at least one compound together with one or more pharmaceutically acceptable excipients.

11. The method of claim 10, which pharmaceutical composition is formulated for oral administration.

12. The method of claim 10, wherein said pharmaceutical composition is formulated as a unit dosage form comprising from 0.1 to about 500 mg of the one or more compounds.

13. The method of claim 9, wherein the compound is represented by formula VII:

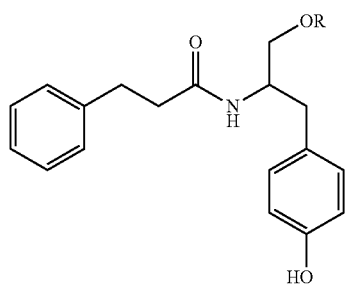

in which R is a polyalkylene glycol polymer having n units, wherein n is 7.

14. The method as claimed in claim 1 for the treatment of somatic pain, wherein said somatic pain originates from a tendon, bone, blood vessel or nerve.

15. The method as claimed in claim 1 for the treatment of visceral pain.

16. The method as claimed in claim 1 for the treatment of phantom limb pain.

17. The method as claimed in claim 1 for the treatment of myofascial pain.

18. The method as claimed in claim 5, wherein n is 1 or 2.

19. The method as claimed in claim 1, wherein the compound is the S-enantiomer.

20. The method as claimed in claim 13, wherein the compound is the S-enantiomer.

* * * * *